(12) United States Patent
Gdovin et al.

(10) Patent No.: US 10,946,096 B2
(45) Date of Patent: Mar. 16, 2021

(54) NITROBENZALDEHYDE PROTON RELEASE FOR MANIPULATION OF CELLULAR ACIDOSIS

(71) Applicant: THE BOARD OF REGENTS OF THE UNIVERSITY OF TEXAS SYSTEM, Austin, TX (US)

(72) Inventors: Matthew Gdovin, Spring Branch, TX (US); Brian O'Grady, Nashville, TN (US); Elma Frias, Riverside, CA (US); Haley Hazlett, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 836 days.

(21) Appl. No.: 15/121,276

(22) PCT Filed: Feb. 26, 2015

(86) PCT No.: PCT/US2015/017862
§ 371 (c)(1),
(2) Date: Aug. 24, 2016

(87) PCT Pub. No.: WO2015/130997
PCT Pub. Date: Sep. 3, 2015

(65) Prior Publication Data
US 2017/0202964 A1   Jul. 20, 2017

Related U.S. Application Data

(60) Provisional application No. 61/944,988, filed on Feb. 26, 2014.

(51) Int. Cl.
*A61K 41/00* (2020.01)
*A61N 5/06* (2006.01)
*A61K 31/192* (2006.01)

(52) U.S. Cl.
CPC ........ *A61K 41/0033* (2013.01); *A61K 31/192* (2013.01); *A61N 5/062* (2013.01); *A61N 2005/0661* (2013.01)

(58) Field of Classification Search
CPC .. A61K 41/0033; A61K 31/192; A61N 5/062; A61N 2005/0661
See application file for complete search history.

(56) References Cited

U.S. PATENT DOCUMENTS

| | | | |
|---|---|---|---|
| 5,965,119 A | 10/1999 | Greenwald et al. | 424/78.7 |
| 6,180,095 B1 | 1/2001 | Greenwald et al. | 424/85.1 |
| 6,303,569 B1 | 10/2001 | Greenwald et al. | 514/1.3 |
| 6,624,142 B2 | 9/2003 | Greenwald et al. | 514/1.3 |
| 6,720,306 B2 | 4/2004 | Greenwald et al. | 514/1.3 |
| 6,824,782 B2 | 11/2004 | Whitlow et al. | 424/178.1 |
| 7,074,770 B1 | 7/2006 | Charo et al. | 514/44 R |
| 7,087,229 B2 | 8/2006 | Zhao et al. | 424/179.1 |
| 7,122,189 B2 | 10/2006 | Zhao et al. | 424/179.1 |
| 7,795,380 B2 | 9/2010 | Rice et al. | 530/300 |
| 2003/0191459 A1 | 10/2003 | Ganz et al. | 606/15 |
| 2006/0199776 A1 | 9/2006 | Blagg | 514/43 |
| 2011/0136132 A1 | 6/2011 | Tseng et al. | 435/7.1 |

FOREIGN PATENT DOCUMENTS

| | | |
|---|---|---|
| JP | S55-69510 | 5/1980 |
| JP | 2003-508124 | 3/2003 |
| JP | 2006-137682 | 6/2006 |
| WO | WO/10/022688 | 3/2010 |

OTHER PUBLICATIONS

Extended European Search Report in European Application No. 15755844.6 dated Aug. 17, 2017.
Lagadic-Gossmann, et al., Cell Death and Differentiation 11:953-61, 2004.
Park, et al., British J Cancer. 80(12):1892-7, 1999.
Almutawa et al., "Current status of photoprotection by window glass, automobile glass, window films, and sunglasses." *Photodermatol Photoimmunol Photomed.* vol. 29, No. 2, 2013, pp. 65-72.
Amaral et al., "The role of p53 in apoptosis." *Discovery Medicine*, vol. 9, No. 45, 2010, pp. 145-152.
Andrade et al., "Plasma membrane and nuclear envelope integrity during the blebbing stage of apoptosis: a time-lapse study." *Biology of the Cell*, vol. 102, No. 1, 2010, pp. 25-35.
Armstrong et al., "Brainstem encephalitis (rhombencephalitis) due to Listeria monocytogenes: case report and review." *Clin. Infect. Dis.* vol. 16, No. 5, 1993, pp. 689-702.
Bartosz et al., "Reactive oxygen species: destroyers or messengers?" *Biochemical Pharmacology*, vol. 77, No. 8, 2009, pp. 1303-1315.
Benaim et al., "Phosphorylation of calmodulin. Functional implications." *Eur J Biochem.* vol. 269, No. 15, 2002, pp. 3619-3631.
Benveniste et al., "Mechanisms of antibiotic resistance in bacteria." *Annual Rev Biochem*, vol. 42, No. 1, 1973, pp. 471-506
Bevers et al., "Phospholipid scramblase: an update." *Federation of European Biochemical Societies Letters*, vol. 584, No. 13, 2010, pp. 2724-2730.
Cardone et al., "The role of disturbed pH dynamics and the Na+/H+ exchanger in metastasis." *Nature Review Cancer.* vol. 5, No. 10, 2005, pp. 786-795.

(Continued)

*Primary Examiner* — Kortney L. Klinkel
*Assistant Examiner* — William Y Lee
(74) *Attorney, Agent, or Firm* — Norton Rose Fulbright US LLP

(57) ABSTRACT

Certain embodiments are directed to photo-activated compounds for the manipulation of pH in a cell. In certain aspects the photo-activated compound is 2-nitrobenzaldehyde (NBA). Photo-activated compounds can be used as a targeted therapy for a variety of disease states and conditions, such as cancer.

14 Claims, 26 Drawing Sheets
Specification includes a Sequence Listing.

(56) References Cited

OTHER PUBLICATIONS

Circu et al., *Free Radical Biology & Medicine*, 2010, 48(6):749-62.
Colombo et al., "HER2 targeting as a two-sided strategy for breast cancer diagnosis and treatment: Outlook and recent implications in nanomedical approaches." *Pharmacol Res*, vol. 62, No. 2, 2010, pp. 150-165.
Davies et al., *Microbiology and Molecular Biology Reviews*, 2010, 74(3):417-33.
De Bruin et al., *Cancer Discov.* 4(5):606-19, 2014.
Del Castillo et al., "Mechanism of the increased acetylcholine sensitivity of skeletal muscle in low pH solutions." *J. Cell Comp Physiol*, vol. 59, 1962, pp. 35-44.
Diaspro et al., "Two-photon fluorescence excitation and related techniques in biological microscopy." *Q Rev Biophys.* vol. 38, No. 2, 2005, pp. 97-166.
Donten et al., "pH jump induced α-helix folding of poly-1-glutamic acid," *Chemical Physics*, vol. 422, 2013, pp. 124-130.
Emde et al., *Crit Rev Oncol Hematol.* 2012, 84 Suppl 1:e49-57.
Fraser et al., *Journal of Physiology*, 2005, 563(3):745-64.
Gabizon et al., "Tumor cell targeting of liposome-entrapped drugs with phospholipid-anchored folic acid-PEG conjugates." *Advanced drug delivery reviews* vol. 56, No. 8, 2004, pp. 1177-1192.
Gabizon et al., "Improved therapeutic activity of folate-targeted liposomal doxorubicin in folate receptor-expressing tumor models." *Cancer Chemother Pharmacol.* vol. 66, No. 1, 2010, pp. 43-52.
Gao et al., "Decreased intracellular pH induced by cariporide differentially contributes to human umbilical cord-derived mesenchymal stem cells differentiation." *Cellular Physiology and Biochemistry*, vol. 33, No. 1, 2014, pp. 185-194.
Garnovskaya et al., *J Biol Chem.* 2003, 278(19): 16908-15.
Giffard et al., "Acidosis reduces NMDA receptor activation, glutamate neurotoxicity, and oxygen-glucose deprivation neuronal injury in cortical cultures." *Brain Res*, vol. 506, No. 2, 1990, pp. 339-342.
Gray et al., *Bacteriol. Rev.* 1966, 30:309-82.
Gupta et al., *Antioxidants & Redox Signaling*, 2012, 16(11):1295-1322.
Idris et al., "In vivo photodynamic therapy using upconversion nanoparticles as remote-controlled nanotransducers." *Nature Medicine*, vol. 18, No. 10, 2012, pp. 1580-1585.
International Preliminary Report on Patentability in International Application No. PCT/US2015/017862 dated Sep. 9, 2016.
International Search Report and Written Opinion in International Application No. PCT/US2015/017862 dated Jun. 10, 2015.
Kim, et al., Mol Cancer. 10:46, 2011.
Kohse, "Photoswitching of enzyme activity by laser-induced pH-jump." *J Am Chem Soc.* vol. 135, No. 25, 2013, pp. 9407-9411.
Köster et al., *J Biol Chem.* 2011, 286(47): 40954-61.
Kularatne et al., *Angwewandte Chemie International Edition*, 2013, 52:12100-103.
Kurahara et al., "Clinical significance of folate receptor β-expressing tumor-associated macrophages in pancreatic cancer." *Annals of surgical oncology*, vol. 19, No. 7, 2012, pp. 2264-2271.
Lamuraglia et al., "Photodynamic therapy of vein grafts: suppression of intimal hyperplasia of the vein graft but not the anastomosis." *Journal of Vascular Surgery*, vol. 21, No. 6, 1995, pp. 882-890.
Mairet-Coello et al., *Neuron*, 2013, 78(1):94-108.
Martindale et al., "Cellular response to oxidative stress: signaling for suicide and survival." *Journal of Cellular Physiology*, vol. 192, No. 1, 2002, pp. 1-15.
McCarty et al., "Manipulating tumor acidification as a cancer treatment strategy." *Alternative Medicine Review*, vol. 15, No. 3, 2010, pp. 264-272.
Miskiewicz et al., "HDAC6 is a Bruchpilot deacetylase that facilitates neurotransmitter release." *Cell Reports*, vol. 8, No. 1, 2014, pp. 94-102.

Orlov et al., "Cell volume and monovalent ion transporters: their role in cell death machinery triggering and progression." *Am J Physiol Cell Physiol.* vol. 305, No. 4, 2013, pp. C361-C372.
Palma et al., "Effects of pH on acetylcholine receptor function." J Membr Biol, vol. 120, No. 1, 1991, pp. 67-73.
Phiel et al., *Journal of Biological Chemistry*, 2001, 276(39):36734-41.
Przepiorka et al., *Blood.* 2002, 95(1):83-89.
Putney et al., "The changing face of the Na+/H+ exchanger, NHE1: structure, regulation, and cellular actions." *Annual Reviews.* vol. 42, 2002, pp. 527-552.
Raghunand et al., *British Journal of Cancer*, 1999, 80(7):1005-11.
Ravindran, et al., J Health Care Poor Underserved. 22(40):174-186, 2011.
Ray et al., *Cellular Signaling* 2012, 24(5):981-90.
Remillard et al., "Activation of K+ channels: an essential pathway in programmed cell death." *Am J Physiol Lung Cell Mol Physiol.* vol. 286, No. 1, 2004, pp. L49-L67.
Ropero et al., "The role of histone deacetylases (HDACs) in human cancer." *Molecular Oncology*, vol. 1, No. 1, 2007, pp. 19-25.
Salazar et al., "The folate receptor: what does it promise in tissue-targeted therapeutics?" *Cancer metastasis reviews*, vol. 26, No. 1, 2007, pp. 141-152.
Schutters et al., *Springer*, 2010, (15):1072-82.
Shabala et al., "Responses of Listeria monocytogenes to acid stress and glucose availability monitored by measurements of intracellular pH and viable counts." *International Journal of Food Microbiology*, vol. 75, No. 1, 2002, pp. 89-97.
Shultz et al., "Kinetics and comparative reactivity of human class I and class IIb histone deacetylases." *Biochemistry*, vol. 43, No. 34, 2004, pp. 11083-11091.
Sliwinska et al., "Photodynamic therapy for polypoidal choroidal vasculopathy." *Prog Retin Eye Res.* vol. 37, 2013, pp. 182-199.
Slonczewski et al., "Cytoplasmic pH measurement and homeostasis in bacteria and archaea." *Advances in Microbial Physiology*, vol. 55, 2009, pp. 1-79.
Smart et al., "A novel effect of zinc on the lobster muscle GABA receptor." Proc R Soc Lond B Biol Sci, vol. 215, No. 1200, 1982, pp. 327-341.
Sweitach et al., *Biophys J*, 2007, 92(2):641-53.
Takeuchi et al., 1967, J Physiol, 1967, 191:575-90.
Tian et al., "Progress of platelet derived grow factor family in non-small cell lung cancer." *Zhongguo Fei Ai Za Zhi.* vol. 17, No. 1, 2014, pp. 42-48.
Tijskens et al., "Modeling the effect of temperature and pH on activity of enzymes: the case of phytases." *Biotechnol Bioeng*, vol. 72, No. 3, 2001, pp. 323-330.
Traynelis et al., "Proton inhibition of N-methyl-D-aspartate receptors in cerebellar neurons." Nature, vol. 345, No. 6273, 1990, pp. 347-350.
Van Dam et al., "Intraoperative tumor-specific fluorescence imaging in ovarian cancer by folate receptor-α targeting: first in-human results." *Nature medicine*, vol. 17, No. 10, 2011, pp. 1315-1319.
Verhoven et al., *Journal of Experimental Medicine*, 1995, 182(5):1597-601.
Wang et al., *Cardiovasc Res* 2013, 98(1):56-63.
Wemmie et al., Neuron, 2002, 34(3):463-77.
Whitelock-Jones et al., "Listeria pneumonia. A case report." *South African Medical Journal*, 1989, 75(4):188-89.
Yi et al., *J. Biol Chem.* 2012, 287(13):10316-24.
Zamora et al., "Intracellular pH (pHi) Measurements in the In Vitro Tadpole Brainstem: Direct Correlations between Changes in pHi and Ventilation," *The Open Zoology Journal*, vol. 6, 2013, pp. 8-17.
Zha et al., Proc Natl Acad Sci USA, 2006, 103(44):16556-61.
Office Action issued in corresponding Japanese Application No. 2016-554590, dated Oct. 24, 2018.
Gottlieb et al., "Apoptosis induced in Jurkat cells by several agents is preceded by intracellular acidification" *Proc. Natl. Acad. Sci. USA.*, 1996; 93: 654-658.
Japanese Office Action issued in Application No. 2016-554590, dated Aug. 1, 2019 (English translation provided).

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Gly Phe Leu Gly
1
```

NITROBENZALDEHYDE PROTON RELEASE FOR MANIPULATION OF CELLULAR ACIDOSIS

This application is a national phase application under 35 U.S.C. § 371 of International Application No. PCT/US2015/017862, filed Feb. 26, 2015 which claims priority to U.S. Provisional Patent Application Ser. No. 61/944,988, filed Feb. 26, 2014. Both applications are hereby incorporated in their entirety.

BACKGROUND

The present invention relates generally to manipulation of pH, and more specifically to the use of nitrobenzaldehyde or its analogs as a treatment for a disease state.

Cancer is defined as a malignant disease involving unregulated cell growth, metastasis throughout the body, and evasion of apoptosis. Due to its rapidly evolving nature, few similarities have been found across different cancers. Present research is currently aimed at the detection and distinction of specific traits, behaviors, and mutations unique to cancers. Current cancer treatments include chemotherapy, radiation, and biological therapy. Classic cancer therapies often require surgery or a combination of therapies for effective treatment. Most treatments that are in use today rely on inhibition of cell division from radiation damage or activation of apoptosis pathways. Newer treatment strategies focus on targeting unregulated proteins, such as HER-2 in breast cancer cells. A limitation to current methods of cancer treatment includes damage to healthy tissue, which in some cases can result in DNA damage, a known cause of cancer. Despite new treatment methodologies, significant changes in immediate cell death have yet to be reported. Cancerous cells that survive treatment, which are responsible for reoccurrence of cancer, are generally more aggressive and resistant to treatment (McCarty and Whitaker, *Alternative Medicine Review*, 2010, 15(3):264-72). Despite advances in the field, cancer mortality rates remain high (American Cancer Society, *Cancer Treatment and Survivorship Facts & Figures 2012-2013*, 2012). There remains a need for additional cancer therapies.

SUMMARY

Certain embodiments are directed to photo-activated compounds for the manipulation of pH in a cell. In certain aspects the photo-activated compound is 2-nitrobenzaldehyde (NBA). NBA can be used to induce apoptosis in a target cell, a targeted apoptosis-based therapy. The targeted apoptosis therapy provides for (i) diffusion and toxicity of a photo-activated compound (e.g., NBA) in a biological system, (ii) induction of focal acidosis, (iii) induction of cellular damage and death in response to a sudden acidosis, and (iv) targeting of cells or tissues of biological systems.

Certain embodiments are directed to a method of treatment for certain diseases through inducing intracellular acidosis. In certain aspects the methods comprise administering NBA to a patient, tissue, or cell; exposing a target tissue or cells to certain wavelengths of light to photo-activate a compound resulting in the uncaging of hydrogen ions and induction of acidosis, apoptosis, and/or cell death. In certain aspects exposure to a light is provided using a "flash paradigm." Light can be provided pulsed or flashed. In certain aspects light is provided in 1, 2, 3, 4, 5, 6, or more flashes. A flash can be for 10, 20, 30, 40, 50, 60, 70, 80, 90, 100 seconds or more, including all values and ranges there between. In certain aspects a flash regime is provided having a first flash of 20, 40, 60, 80, or 100 seconds; a second flash of 10, 20, 30, 40, 50, or 60 seconds; and a third flash of 20, 40, 60, 80, 100 seconds. The intervals between flashes can be 1, 1.5, 2, 2.5, 3, 3.5, 4 or more minutes, including all values and ranges there between. In certain embodiments there are about 2 minute intervals between each flash. In further aspects the flash regime can be a first 60 second flash followed by a 2 minute interval, a second 30 second flash followed by a 2 minute interval, and a third 60 second flash (60-30-60). Ranges of exposure time as well as power of various light sources may be utilized under any combination of effective time intervals and exposure to induce various magnitudes of intracellular acidification.

In certain aspects the light is ultraviolet (UV) light. In a further aspect the UV light will have a wavelength in the range of 200 to 400 nm. In certain aspects the light will have a wavelength of 350 nm. The light source can be a laser or non-laser light source.

In certain embodiments the photo-activated compound is administered systemically in combination with a targeted light exposure. In other aspects the photo-activated compound is administered locally. In certain aspects the photo-activated compound is administered using a needle, endoscope, cannula, catheter or other appropriate medical device for the target site. In a further aspect the photo-activated compound is administered topically if the target tissue is the skin. In certain aspects the photo-activated compound is NBA or a functional analog thereof.

NBA is a small molecule that has a high likelihood of crossing cellular and bacterial membranes. Uncaging hydrogen ions by UV activated NBA causes damage by inducing cell wide acidosis in eukaryotic cells. The ability to damage a wide range of proteins and enzymatic processes inside a pathogen, e.g., bacterium, reduces the chances of the evolution of resistance compared to traditional antibiotics. In some embodiments NBA is administered and photo-uncaged to manipulate the activity of intracellular processes by the activation or deactivation of enzymes and proteins through modulation of $pH_i$, and subsequent cellular function, which does not necessarily entail the death of the cell or tissue into which NBA is administered and photo-caged or photo-activated. In some embodiments, uncaged $H^+$ from NBA or similar compound will be utilized in order to attain a desired intracellular pH for the activation of cellular dedifferentiation of stem cell lines (Gao et al., *Cellular Physiology and Biochemistry*, 2014, 33(1):185-94).

In some embodiments for the local treatment of internal tissues and cancers, the light may be targeted to specific tissues with the use of an external light source, or an internal light source. In certain aspects the light can be focused or targeted to a defined location. Internal light sources may include an endoscope, a fiber-optic light source, an implantable illuminator, or a source of chemiluminescence such as luminol.

In other embodiments a photo-activated compound can be used to kill or impede the growth of microorganisms, including, but not limited to bacteria, fungi, and amoebas. The ability to kill microorganisms with the compounds and methods described herein has applications as a cleaning or sterilization agent, particularly in applications such as point of injury care, mass casualty management, and natural disaster situations. A surface or object to be sterilized can be contacted with the photo-activated compound. The contacted surface or object is then expose to an appropriate light source comprising a wavelength that activates or uncages the compound.

Other embodiments of the invention involve the use of nanoparticles. Such nanoparticles may vary in rare earth metal-doped upconverting cores, hydrophilic biocompatible polymers, compound (e.g., NBA) loading concentrations and silica loading times. In certain aspects a nanoparticle comprise a compound (e.g., NBA) coupled (directly or via linker) to a particle (e.g., a $KYb_2F_7$ core). In certain aspects particles with a $KYb_2F_7$ core showed very high efficacy in vitro with minimal peripheral damage. Nanoparticles can be constructed of various cores ranging in diameter from approximately 50-100 nm. Nanoparticles may be selected based upon upconversion spectra that are collected for each core to test the best ultraviolet emission revealing maximum uncaging. Photon upconversion or upconversion (UC) is a process in which the sequential absorption of two or more photons leads to the emission of light at shorter wavelength than the excitation wavelength. It is an anti-Stokes type emission. An example is the conversion of infrared light to visible light. Materials by which upconversion can take place often contain ions of d-block and f-block elements (e.g., $Ti^{2+}$, $Ni^{2+}$, $Mo^{3+}$, $Re^{4+}$, and $Os^{4+}$). In certain aspects a nanoparticle is imaged using a transmission electron microscope (TEM) and tested for its zeta potential.

Various biocompatible polymers, such as PEG, polyvinylpyrrolidone, and photo linkers, may be conjugated to the nanoparticle in order to allow for the most efficient loading and cellular uptake of NBA and/or other uncaging compounds, such as calcium. Silica may be used to protect the polymers from extra- or intracellular interactions that may cause cell toxicity and/or degradation. The use of silica may also be employed to further reduce the zeta potential on the nanoparticle for the increase of cellular uptake. Various surfactants, antibodies, or ligands can be applied to the nanoparticles for targeted therapies. All combinations of the previously mentioned may be tested in vitro and in vivo for the overall efficacy of the nanoparticle in a plated condition and in a living animal for long-term effects.

Other methods of targeting nanoparticles to specific tissues or cancer may also be applied. Targeting may be through passive targeting based phenomenon such as the enhanced permeation and retention effect, caused by leaky angiogenic vessels and poor lymphatic drainage that has been used to explain why macromolecules and nanoparticles are found at higher ratios in tumors compared to normal tissues. Targeting may also be accomplished by active targeting in which ligands are coupled to the nanoparticle that correspond to molecules found exclusively in cancer cells, or which are found in greater abundance in cancer cells.

The ability to effectively target specific cells in a focal manner is a promising therapeutic delivery mechanism. Cancer cells can exhibit a variety of unique characteristics that can be targeted for the focal delivery of a therapeutic. Delivery mechanisms designed to target specific cancer cells offer the ability to reduce toxic side effects usually associated with chemotherapeutic treatment (Gabizon et al., *Advanced drug delivery reviews* 2004, 56:1177-92). The wide array of possible targets for cancer include surface receptors such as human epidermal growth factor receptor 2 (Emde et al., *Crit Rev Oncol Hematol*. 2012, 84 Suppl 1:e49-57; Colombo et al., *Pharmacol Res* 2010, 62(2):150-65), folate receptors (Salazar et al., *Cancer metastasis reviews*, 2007, 26:141-52), and estrogen receptors (Kleinsmith et al., "Cancer screening, diagnosis, and treatment", in Principles of Cancer Biology. Pearson Education, Inc., 2006; 218-224). Other possible targets for therapeutic delivery mechanisms include cytokines (Przepiorka et al., *Blood*, 2002, 95(1):83-89; Kleinsmith et al., "Cancer screening, diagnosis, and treatment", in Principles of Cancer Biology. Pearson Education, Inc., 2006; 218-224) and growth factors (de Bruin et al., *Cancer Discov.* 2014; Wang et al., *Cardiovasc Res* 2013, 98(1):56-63). A more comprehensive list of possible targets can be found on Table 1.

TABLE 1

Potential targets for cancer therapy

| Target | Cancer(s) | Citations |
| --- | --- | --- |
| Epidermal Growth Factor (EGF) | Lung cancer | de Bruin et al., *Cancer Discov.* 2014 |
| Fibroblast Growth Factor (FGF) | Non-small-cell lung cancer | Wang et al., *Cardiovasc Res* 98(1): 56-63 |
| Platelet-derived Growth Factor (PDGF) | Non-small-cell lung cancer | Tian et al., *Zhongguo Fei Ai Za Zhi*. 2014, 17(1): 42-48 |
| Vascular Endothelial Growth Factor (VEGF) | Breast, ovaria, lung, gastric, colorectal | Kleinsmith et al., in *Principles of Cancer Biology*. Pearson Education, Inc., 2006: 218-24 |
| TNF-α | Hairy cell leukemia | Kleinsmith et al., Id. |
| TNF-β | Kaposi's sarcoma | Kleinsmith et al., Id. |
| CD20 | Non-Hodgkin's B cell lymphoma | Kleinsmith et al., Id. |
| Estrogen Receptor | Breast cancer | Kleinsmith et al., Id. |
| human epidermal growth factor receptor 2 (HER2) | Breast cancer | Emde et al., *Crit Rev Oncol Hematol*. 2012, 84 Suppl 1: e49-57; Colombo et al., *Pharmacol Res* 2010, 62(2): 150-65 |
| Folate Receptor-α | Epithelial cancer (non-mucinous adenocarcinomas of ovary, uterus and cervix, ependymal brain) | Kularatne et al., *Angwewandte Chemie International Edition*, 2013, 52: 12100-103; Salazar et al., *Cancer metastasis reviews*, 2007, 26: 141-52; van Dam et al., *Nature medicine* 2011, 17: 1315-19 |

TABLE 1-continued

Potential targets for cancer therapy

| Target | Cancer(s) | Citations |
| --- | --- | --- |
| Folate Receptor-β | Chronic and acute myelogenous leukemia; pancreatic cancer-associated macrophages | Kularatne et al., *Angwewandte Chemie International Edition*, 2013, 52: 12100-103; Salazar et al,. *Cancer metastasis reviews*, 2007, 26: 141-52; Kurahara et al., *Annals of surgical oncology* 2012, 19: 2264-71 |
| Interleukin-2 | Kidney cancer and melanoma | Przepiorka et al., *Blood*. 2002, 95(1): 83-89 |
| BCR-ABL* | Chronic myelogenous leukemias | Kleinsmith et al., in *Principles of Cancer Biology*. Pearson Education, Inc., 2006: 218-24 |

Other embodiments of the invention are discussed throughout this application. Any embodiment discussed with respect to one aspect applies to other aspects as well and vice versa. Each embodiment described herein is understood to be embodiments that are applicable to all aspects of the invention. It is contemplated that any embodiment discussed herein can be implemented with respect to any device, method, or composition, and vice versa. Furthermore, systems, compositions, and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
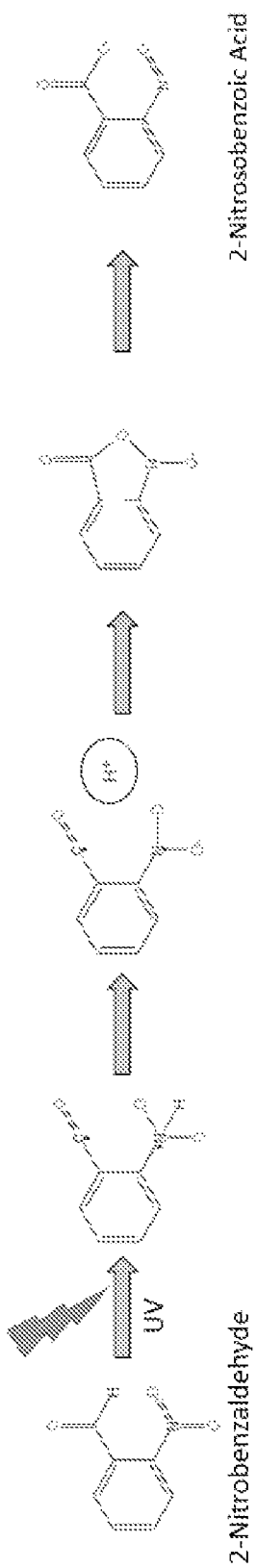
FIG. 1 is a diagram illustrating the conversion of 2-nitrobenzaldehyde (NBA) to 2-nitrosobenzoic acid. The diagram also illustrates the reaction mechanism that ensues with exposure of NBA to ultraviolet (UV) light at a wavelength of 350 nm. NBA exposure to 350 nm UV light results in the release of protons and the formation of 2-nitrosobenzoic acid.

Most cancers can be characterized by an excessive production and extrusion of lactic acid via aerobic glycolysis known as the Warburg Effect. The excessive production of intracellular acid is effectively extruded by cancer cells resulting in an acidic extracellular environment, which has been directly linked to metastatic potential (McCarty and Whitaker, *Alternative Medicine Review*, 2010, 15(3):264-72). Extracellular acidosis results in an increased rate of blood-vessel formation, or angiogenesis, at the site of a tumor, as well as decreased effectiveness of most chemotherapeutic drugs, which are alkaline in nature. In order to survive in this acidic environment, cancer cells express or up-regulate proton exchangers, most notably sodium/hydrogen exchanger 1 (NHE1), which extrude protons and maintain a slightly alkaline intracellular pH ($pH_i$).

While an excessive amount of acid production and upregulation of NHE1 contributes to tumor aggressiveness, that same excessive extrusion could also be turned against cancer cells as a form of treatment. Due to the inherent challenges of selectively treating only NHE1 in cancer cells, direct disruption of pH, has been the elusive target of cancer therapies since the discovery of the Warburg Effect in 1931. NHE1 blockers, such as amiloride-based drugs, act to kill cancer by trapping protons inside and subsequently dropping pH, to induce apoptosis. Other experimental techniques that implement pH manipulation include alkalization of the extracellular space with sodium bicarbonate-laced drinking water, or increasing oxygen perfusion to the tumor mass itself (Raghunand and Gillies, *British Journal of Cancer*, 1999, 80(7):1005-11).

As with many chemotherapeutic approaches, NHE1 blockers are not focally restricted to the tumor site, causing systemic damage to peripheral tissue due to the ubiquitous distribution of NHE1 on all living cells. Alternate forms of intracellular acidification, such as $NH_4Cl$ prepulse (Zamora et al., *The Open Zoology Journal*, 2013, 6:8-17) are not focal, difficult to implement, cytotoxic, and time consuming.

2-nitrobenzaldehyde ("NBA") is a photoactivated molecule capable of immediately releasing a proton upon exposure to 350 nm ultraviolet (UV) light (Ravindran et al., *Cellular Signaling* 2012, 24(5):981-90). NBA passively diffuses through the cellular membrane and becomes trapped due to the slight positive charge on the molecule. Once inside the cell, NBA is capable of remaining inactive and intact until excited by UV light (200 nm to 410 nm, Diaspro et al., *Q Rev Biophys*. 2005, 38(2):97-166). NBA has been used to induce a focal, rapid intracellular acidosis, resulting in intrinsic apoptosis of the target cell. Due to the ease of entry into the cell, the tendency of the molecule to remain inside of the cell, the nontoxic nature of the molecule, and the instant acidification upon exposure to UV light, NBA is an ideal mechanism for disruption of $pH_i$. The fast, focal disruption of $pH_i$ regulation in cancer cells is an untapped method of cancer treatment that holds great potential as an alternate to chemotherapy and radiation. In addition, treatment is not "cancer-specific" and can be used in treating a myriad of cancers, such as multi-drug resistant (MDR) cancers.

I. Nanoparticles

Photodynamic therapy (PDT) is one of the fastest growing modalities for treating many types of cancers. This technology is in its infancy and currently is not effective enough to nullify the need for more effective treatments such as surgery or chemotherapy. PDT has been utilized as a treatment for other diseases such as vein grafts to limit intimal hyperplasia post-surgery (Lamuraglia et al., *Journal of Vascular Surgery*, 1995, 21(6):882-90), psoriasis (Almutawa et al., *Photodermatol Photoimmunol Photomed*. 2013), and polypoidal choroidal vasculopathy (Sliwinska et al., *Prog Retin Eye Res*. 2013, 37:182-99). However, the most promising application for PDT is its use in oncology. PDT applied to cancer cells in vitro and in vivo has shown cell death as high as 60% (Idris et al., *Nature Medicine*, 2012, 18(10): 1580-85). Currently, one of the most effective uses of PDT employs the photoactivation of a nanoparticle to cause intracellular release of reactive oxygen species (ROS) for cancer cell therapy (Idris et al., *Nature Medicine*, 2012, 18(10):1580-85).

Unlike their more stable elemental oxygen counterpart, ROS consist of radical and non-radical oxygen species that are capable of intracellular protein regulation through redox reactions (Bartosz et al., *Biochemical Pharmacology*, 2009, 77(8):1303-15; Circu et al., *Free Radical Biology & Medicine*, 2010, 48(6):749-62). Endogenously produced by the mitochondria, ROS are involved in a wide array of intracellular signal regulation, from cell proliferation and gene regulation to mitochondrial oxidative stress and apoptosis (Ray et al., *Cellular Signaling* 2012, 24(5):981-90). ROS can contribute to the activation of an apoptotic death cascade by opening a permeability transition pore complex to allow for the activation of apoptosis-inducing factors such as cytochrome c and caspase (Martindale et al., *Journal of Cellular Physiology*, 2002, 192(1):1-15; Gupta et al., *Antioxidants & Redox Signaling*, 2012, 16(11):1295-1322).

A nanoparticle was constructed to improve PDT in B16-0 melanoma cancer cells by utilizing a dual-photosensitizing nanoparticle to enhance cell death from the photoactivation of ROS (Idris et al., *Nature Medicine*, 2012, 18(10):1580-85). This particular nanoparticle had a $NaYF_4$ crystal core uniformly coated in mesoporous silica for the in vitro experiments. Each nanoparticle was loaded with Merocyanine 540 (MC540) and Zinc (II) Phthalocyanine (ZnPc), both of which are photosensitizing drugs that are only activated when introduced to visible light. Upon the upconversion of 980 nm near infrared light (NIR) to visible light, MC540 and ZnPc release ROS and induce subsequent cellular damage (Idris et al., *Nature Medicine*, 2012, 18(10): 1580-85). To test the efficacy of the ROS treatment, the coated nanoparticles were conjugated with folic acid and polyethylene glycol (PEG) to facilitate movement across the cell membrane. The nanoparticles were combined with cultured melanoma cancer cells to facilitate endocytosis, which were then injected into C57BL/6 mice. The PDT and subsequent release of ROS was successful in reducing tumor size and increasing apoptosis in vivo.

Cancer cell death (63%) and tumor size reduction reported by Idris et al. (2012) are insufficient to be considered as a successful clinical treatment. This percentage of cell death is not high enough to stop uncontrollable cell proliferation and avoid additional treatments, such as surgery and chemotherapy, to remove remaining cancer cells. This particular nanoparticle also was not loaded into the tumor after a mass had formed. Rather, the cancer cells were grown in vitro and loaded with the nanoparticles before being introduced to the mouse. Culturing cancer cells with a PDT nanoparticle prior to introducing them in vivo, although moderately successful, is not a realistic approach for treatment analogous to treatment in humans.

The proton donor NBA will diffuse across the cell membrane and remain in the intracellular space. Facilitation of the cellular entry of NBA is based upon the creation of an extracellular gradient, thereby allowing NBA to passively diffuse through the cell membrane into the intracellular space. The greater electronegativity of oxygen creates a polar carbonyl group and a relatively large molecular dipole moment. The non-bonding electron pairs of oxygen make aldehydes hydrogen-bond acceptors, thereby increasing their water solubility. Removal of NBA from the extracellular space does not result in an efflux of NBA, due primarily to NBA's increased solubility inside the cell.

Effective concentrations of intracellular NBA are not cytotoxic and do not disrupt cellular function. Kohse et al., (*J Am Chem Soc.* 2013, 135(25):9407-11) photo activated the enzyme acid phosphatase from pH 8.0 to 6.0 by the activation of a pH jump using flash photolysis of NBA and did not report any degradation of enzyme function as result of exposure to NBA. Flash photolysis of NBA to reduce pH, of rat ventricular myocytes (Swietach et al., *Biophys J*, 2007, 92(2):641-53) did not alter the $H^+$ buffer capacity of these cells. More importantly, in the absence of UV exposure, NBA (1 mM) did not alter diastolic $Ca^{2+}$, cellular contraction, or "the mechanisms of spatial pH, regulation". The inventors recently loaded the entire in vitro tadpole brainstem with 10 μM NBA and observed no disruption in the spontaneous, fictive respiratory motor output or central respiratory chemoreceptor responses, indicating that at this concentration, NBA does not exert cytotoxic effects on cells which compose the respiratory neural circuits (Ravindran et al., *Journal of Health Care for the Poor and Underserved*, 2011 22(4):174-86).

II. Cellular Pathways and Apoptosis Mechanisms

The ability to effectively target specific cells in a focal manner is a promising therapeutic delivery mechanism. Cancer cells can exhibit a variety of unique characteristics, which can be targeted for the focal delivery of a therapeutic. Delivery mechanisms designed to target specific cancer cells offer the ability to reduce toxic side effects usually associated with chemotherapeutic treatment (Gabizon et al., *Cancer Chemother Pharmacol.* 2010, 66(1):43-52). The wide array of possible targets for cancer include surface receptors such as human epidermal growth factor receptor 2 (Emde et al., *Critical reviews in oncology/hematology* 2012, 84:49-57; Colombo et al., *Pharmacol Res* 2010, 62(2):150-65), folate receptors (Salazar et al., *Cancer metastasis reviews*, 2007, 26:141-52), and estrogen receptors (Kleinsmith et al., in Principles of Cancer Biology. Pearson Education, Inc., 2006, 218-24). Other possible targets for therapeutic delivery mechanisms include cytokines (Przepiorka et al., *Blood.* 2002, 95(1):83-89; Kleinsmith et al., in Principles of Cancer Biology. Pearson Education, Inc., 2006, 218-24), growth factors (de Bruin et al., *Cancer Discov.* 2014; Wang et al., *Cardiovasc Res* 2013, 98(1):56-63), and other cellular pathways and mechanisms.

A. Sodium Hydrogen Exchanger 1 (NHE1)

The sodium hydrogen exchanger 1 (NHE1) is a ubiquitously expressed ion transporter that is highly conserved genetically. NHE1 facilitates the exchange of extracellular $Na^+$ for intracellular $H^+$, promotes hypotonicity, and increases cell volume. NHE1 is characterized by a highly variable intracellular C-terminus, which can be modulated to mediate cellular behaviors including adhesion, morphology, migration, and proliferation (Putney et al., *Annual Reviews.* 2002, (42):527-52). NHE1 is a vital transporter for cell survival.

NHE1 is modulated by many mediators in the cell. Calmodulin (CaM) is a messenger protein that, once bound by calcium or phosphorylated, activates NHE1 via the intracellular regulatory domain (Köster et al., *J Biol Chem.* 2011, 286(47):40954-961). Once bound, NHE1 will be constitutively activated until CaM is unbound. Upon cell volume loss, phosphorylated Janus kinase II will phosphorylate CaM, which then activates NHE1. Activation of NHE1 will cause sodium influx and a concomitant water entry into the cell in an effort to reestablish cell volume. NHE1 is often dimerized with the sodium calcium exchanger 1 (NCX1), which normally transports $Na^+$ into the cell and $Ca^{2+}$ out of the cell. When intracellular $Na^+$ levels rise, the NCX1 reverses the direction of ion transport to prevent further increases in intracellular $Na^+$. The dimerization of NHE1 and NCX1 is normally utilized to modulate osmotic pressure. NHE1 is upregulated in cancer cells, contributing to the effectiveness of $pH_i$ regulation, tumor invasiveness, and avoidance of $pH_i$-induced apoptosis (Cardone et al., *Nature Review Cancer.* 2005, 5(10):786-95).

B. Phosphatidylserine

Phosphatidylserine (PS) is a membrane phospholipid that is normally sequestered to the interior leaflet of a cell's phospholipid bilayer. The expression of PS on the outer surface of the cell membrane has two causes, the lack of membrane asymmetry maintenance by adenosine triphosphate-dependent aminophospholipid translocase, and the activation of lipid scramblases that quickly flip PS to either membrane surface (Verhoven et al., *Journal of Experimental Medicine*, 1995, 182(5):1597-601).

Scramblases are not yet identified and may be one or several proteins that can be activated by at least two pathways. All nucleated human cells have an apoptotic pathway that lead to the expression of PS on the outer membrane surface. Hematopoietic cells also have a reversible, calcium-dependent pathway for expressing PS; non-nucleated erythrocytes have only this calcium-dependent path (Bevers & Williamson, *Federation of European Biochemical Societies Letters*, 2010, 584(13):2724-30). The apoptotic pathway utilizes the collapse of lipid asymmetry to expose PS to the extracellular space as a signal for non-inflammatory phagocytotic removal.

Early in the apoptotic pathway, aminophospholipid translocase is downregulated (Verhoven et al., *Journal of Experi-*

*mental Medicine,* 1995, 182(5):1597-601). Then, once mitochondrial outer membrane permeabilization (MOMP) occurs, scramblase will proceed to transport PS to the outer membrane leaflet. Apoptosis inhibitors acting on the pathway before MOMP occurs can prevent PS expression. Conversely, inhibitors acting after MOMP will block downstream apoptotic events, but PS expression will still occur (Bevers & Williamson, *Federation of European Biochemical Societies Letters,* 2010, 584(13):2724-30).

PS expression in non-hematopoietic cells is a definitive indicator of cell death and can be shown by labeling with fluorescently conjugated Annexin V, a naturally occurring protein with a high affinity for PS. Because PS can also be exposed when a cell membrane loses integrity, a secondary dye that becomes trapped in the membrane can be used to verify that PS exposure is due only to the apoptotic route (Schutters & Reutelingsperger, Springer, 2010, (15):1072-82).

C. P53 and Bcl-2

TP53 is a multifaceted gene involved in a complicated, yet common, pathway. The regulatory network of P53 is studied for its most common occurrences in pathological conditions, such as neurological degeneration, atherosclerosis and cancer (Amaral et al., *Discovery Medicine,* 2010, 9(45):145-52). The most commonly seen causes of cancer are due to damage or deletion of the TP53 gene (Olivier et al., *Cold Spring Harbor Perspectives in Biology,* 2010, 2:1-17). Mutations to this gene are the cause of over 50% of cancers seen today (Kleinsmith, "Cancer screening, diagnosis, and treatment", in Principles of Cancer Biology. Pearson Education, Inc., 2006, 218-24).

The TP53 gene, located on chromosome 17 in humans, is critical for the regulation of the cell cycle. TP53 has been described as a tumor suppressing gene for its role in preventing damaged or mutated DNA from replicating out of control, causing cancer. P53 is upregulated when the cell detects DNA damage, hypoxic conditions, or irregularities in the cell cycle. Under normal conditions P53, can pause the cell cycle and allow for DNA repair mechanisms to fix the damage and resume the cell cycle when fixed, or cause the cell to go immediately into apoptosis. There are many pathways for P53 to induce mitochondrial apoptosis, but one of the most direct routes is the induction of Bax, a proapoptotic protein. Bax binds directly to the mitochondria, causing the release of cytochrome c. When P53 is mutated or deleted, the anti-apoptotic protein Bcl-2 can sequester and further block the functionality of P53. This blockage of the actions of P53 allows for cancer progression regardless of DNA damage or cell cycle malfunction. Another route for cancer progression is the over expression of Bcl-2, leading to the sequestration of all P53 being transcribed and ultimately blocking the apoptotic cascade (Olivier et al., *Cold Spring Harbor Perspectives in Biology,* 2010, 2:1-17).

D. Jak-2 and CaM

When MCF-7 cells are introduced to our unique treatment, the loss of cell volume is observed as early as 3 minutes into treatment. Cell volume decrease has been observed in the first stages of apoptosis (Orlov et al., *Am J Physiol Cell Physiol.* 2013, 305(4):C361-372), and has been attributed to the enhanced activation of water permeable channels (Remillard et al., *Am J Physiol Lung Cell Mol Physiol.* 2004, 286(1):L49-67). In addition, when $H^+$ is uncaged during our novel treatment, NBA undergoes photochemical rearrangement into 2-nitrosobenzoic acid (Diaspro et al., *Q Rev Biophys.* 2005, 38(2):97-166). The increase in $H^+$ combined with the decrease in intracellular $H^+$ buffering constituents would also contribute to decreases in cell volume (Fraser et al., *Journal of Physiology,* 2005, 563(3): 745-64). This intracellular water shedding causes many intracellular regulatory proteins to respond and activate mechanisms to counter the loss of water. One regulatory pathway that is rapidly activated by the water loss and subsequent decrease in cell volume is the JAK/STAT pathway, specifically Janus kinase II (Jak2).

In response to cellular volume loss, Jak2 is activated through phosphorylation. Jak-2 activation can cause phosphorylation of calmodulin (CaM) (Benaim and Villalobo, *Eur J Biochem.* 2002, 269(15):3619-31), which binds to the intracellular C-terminus of NHE1 to constitutively activate it. This activation of NHE1 rapidly increases the intracellular concentration of $Na^+$, causing cell volume recovery though the recruitment of water to the cytosol.

Calmodulin is a second messenger protein found in eukaryotic cells. CaM is involved in a variety of process, including the mechanical increase in activation of NHE1 (Garnovskaya et al., *J Biol Chem.* 2003, 278(19):16908-15). The affinity of CaM to the C-terminus of NHE1 can be increased by either the phosphorylation or calcification of CaM (Garnovskaya et al., *J Biol Chem.* 2003, 278(19): 16908-15; Köster et al., *J Biol Chem.* 2011, 286(47):40954-61).

E. Microorganisms

Bacterial resistance to antibiotics presents an ongoing challenge to health care. The majority of resistance is due to enzymatic adaptations that allow bacteria to degrade antibiotics before affecting their target (Benveniste et al., *Annual Reviews,* 1973, 42:471-506). Once this enzymatic action is developed, it can be quickly transferred from one organism to another through transformation, defeating the effectiveness of drugs. Other methods of resistance include the bacteria's ability to hinder the uptake of antibiotics, as seen with tetracycline and sulfonamide, or a change in the target as with *Staphylococcus aureus* adapting ribosomes to confer resistance to erythromycin (Davies and Davies, *Microbiology and Molecular Biology Reviews,* 2010, 74(3): 417-33). Simple, single-target and single-structure advances in antibiotics require similarly simple defensive adaptations to be performed in these organisms to exhibit a resistance.

Bacteria are a diverse group of organisms that can live in a wide range of environments including extreme ranges of pH. Alkaliphiles may thrive in a range of extracellular pH from 7.5-10.6, and acidophiles may grow easily at pH 1.0-8.0; however, the internal pH of even these extremophiles is much closer to neutral, with an internal pH of 7.5-8.3 and 6.0-7.0 respectively (Slonczewski et al., *Advances in Microbial Physiology,* 2009, 55:1-79). To maintain these exceptional differences in pH, membrane lipids allow bacterial species to be varyingly impermeable to proton movements. Other methods of controlling internal pH include coupling down-gradient ion exchange with upgradient proton exchange such as the $Na^+/H^+$ antiporter of *Escherichia coli*; metabolic switching which makes neutral or acidic products; and various buffering systems (Slonczewski et al., *Advances in Microbial Physiology,* 2009, 55:1-79). For example, *Listeria monocytogenes,* a bacteria responsible for fatal infections associated with processed foods (Shabala et al., *International Journal of Food Microbiology,* 2002, 75:89-97), encephalitis (Armstrong and Fung, *Clin. Infect. Dis.* 1993, 16(5):689-702), pneumonia (Whitelock-Jones et al., *South African Medical Journal,* 1989, 75 (4): 188-89), septicemia (Gray and Killinger, *Bacteriol. Rev.* 1966, 30:309-82), meningitis (Gray and Killinger, *Bacteriol. Rev.* 1966, 30:309-82), intrauterine, and cervical infection in pregnant women which may lead to spontaneous abortions, maintains its pHi between 7.6 to 8.0, and "failure to maintain pHi homeostasis leads to loss of cell viability and, therefore, may be used as a sensitive indicator of the bacterial death at the cellular level" (Shabala et al., *International Journal of Food Microbiology*, 2002, 75:89-97). Vacuolar-type $H^+$-ATPase (V-ATPase) in bacteria and fungi maintain important intracellular proton gradients in organelles such as endosomes and lysosomes that are important in driving calcium uptake via the $H^+/Ca^{2+}$ antiporter. It is possible that significant intracellular and/or intra-organelle acidosis via our NBA treatment would severely disrupt not only acidity, but also important processes necessary for pathogenesis.

F. Enzymatic Activity

Metabolic disorders have plagued society for centuries. Recent advances in science have shown over-active enzymes are one of many causes of these diseases; however, the pathophysiology of metabolic disorders is poorly understood (Mairet-Coello et al., *Neuron*, 2013, 78(1):94-108). Alzheimer's disease is one of the most prevalent forms of dementia, affecting over 5 million people in the United States, and is caused by hyperactivity of cellular enzymes (Mairet-Coello et al., *Neuron*, 2013, 78(1):94-108). In vivo studies have shown that hyperphosphorylation of the microtubule-associated protein Tau by the AMP-activated kinase (AMPK) leads to loss of neuronal spines used for excitatory synaptic transmission (Mairet-Coello et al., *Neuron*, 2013, 78(1):94-108). Reducing the activity of this kinase, pharmacologically or through genetic deletion, showed neuronal spines were not subjected to the snyaptotoxic over-phosphorylation of Tau and had protective effect on hippocampal neurons (Mairet-Coello et al., *Neuron*, 2013, 78(1):94-108).

Enzyme kinetics is a well-studied area of science and has developed many empirical models regarding enzyme functionality in various conditions. One of these models is used to describe and predict the activity of enzymes as a function of pH (Tijskens et al., *Biotechnol Bioeng*, 2001, 72(3):323-30). Most enzymes function within the biological range, a pH between 6 and 8, and have an optimal pH in which their functions are greatest. However, these functional interactions reduce when pH is altered. With significant decreases in $pH_i$, enzymes begin to unfold due to protonation of functional groups and the dissociation of hydrogen bonds, which reduces their activity (Tijskens et al., *Biotechnol Bioeng*, 2001, 72(3):323-30. Donten and Hamm (*Chemical Physics*, 2013, 422:124-30) applied pH "jumps" by administering femtosecond pulses of UV light to NBA to alter the rate and magnitude of folding of poly-L-glutamic acid. While Donten and Hamm (2013) were successful in inducing protein folding, they produced acidic solutions in the test cuvette as low as pH 4.0, which would cause intracellular damage and/or apoptosis. Using the uncaging technique described herein to reduce the pH, of cells will permit the alteration of the activity of many proteins, such as AMPK. This reduction in AMPK activity will reduce the synaptotoxic effects of hyperphosphorylated Tau and stave off the progression of Alzheimer's and other metabolic diseases due to hyperactive enzymes. The use of an NBA nanoparticle will allow for very focal and graded decreases in $pH_i$ in vivo.

Figure 15:
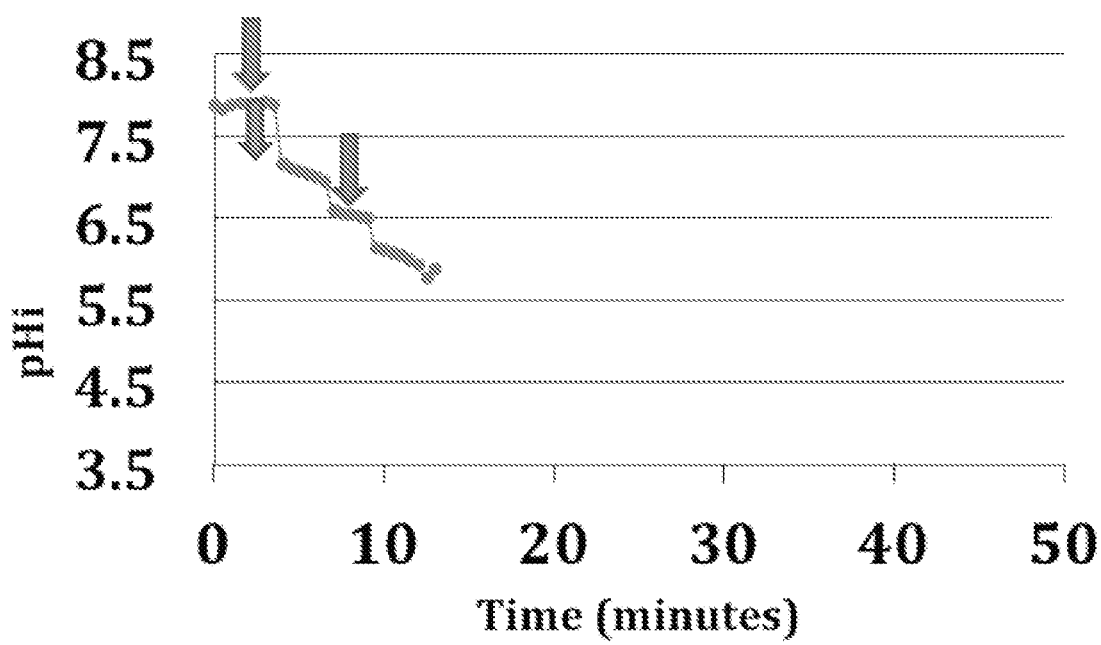
FIG. 15 illustrates optical recordings of the average pH$_i$ of PC12 cells (n=22) over time in response to flash photolysis of NBA. The cells received a 60-30-60 UV flash paradigm at each of the downward arrows. The average pH$_i$ drop for each flash was 0.72, 0.36, 0.36, respectively.
Figure 16:
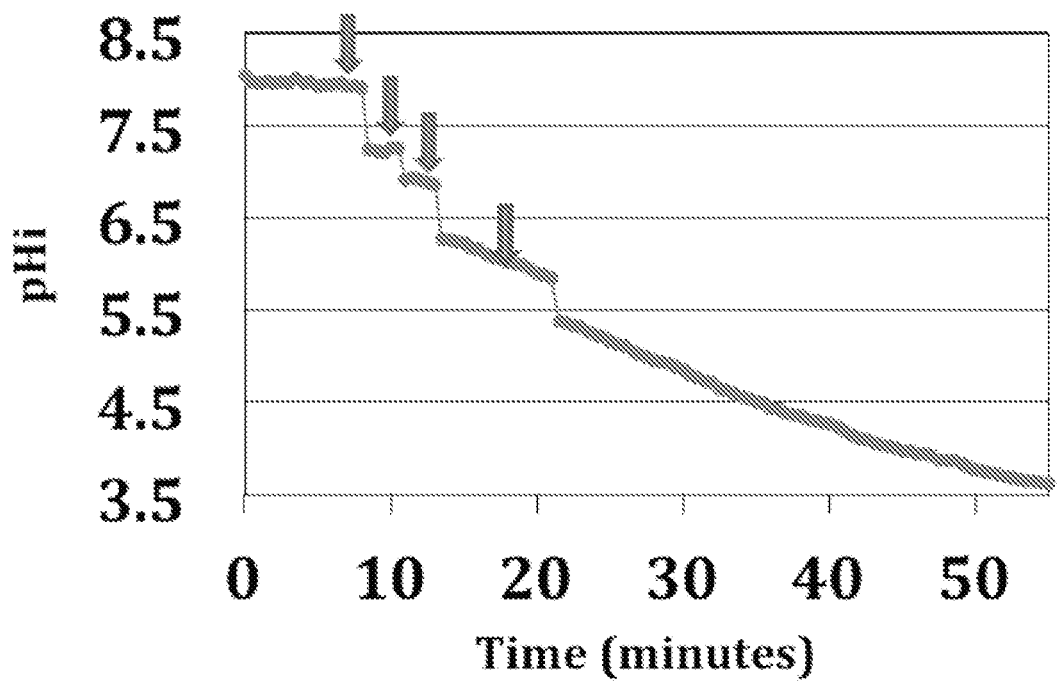
FIG. 16 illustrates optical recordings of the average pH$_i$ of MCF-7 cells (n=13) over time in response to flash photolysis of NBA. The cells received a 60-30-60 UV flash paradigm at each of the downward arrows. The average pH$_i$ drop for each flash was 0.68, 0.35, 0.59, respectively.

Histone deacetylases (HDAC) are a family of enzymes that remove acetyl groups from the amino acid lysine on a histone, thereby increasing the charge on the histone tail. This increase in charge on the histone tail promotes the high-affinity binding between the histones and DNA, leading to a more condensed DNA and prevention of transcription. Currently, 11 HDAC genes have been described (Shultz et al., *Biochemistry*, 2004, 43:11083-91) and their activity has been linked to conditions such as Amyotrophic Lateral Sclerosis (ALS) (Miskiewicz et al., *Cell Reports*, 2014, 8:94-102), gastric, prostate, colon, breast, cervical and gastric cancer (Ropero and Estellar, *Molecular Oncology*, 2007, 19-25). In contrast, histone acetylation neutralizes histone charges and decreases histones ability to bind to DNA. This decrease in histone binding promotes chromatin expansion and gene transcription, such as the activation of the tumor suppressor gene P53 (Phiel et al., *Journal of Biological Chemistry*, 2001, 276(39):36734-41). Although the inhibition of HDACs by valproic acid and trichostatin A (TSA) have been effective in the treatment of epilepsy, the precise mechanisms of action are unknown (Phiel et al., *Journal of Biological Chemistry*, 2001, 276(39):36734-41). Shultz et al., (2004) reported the optimal pHi range for maximum catalytic efficiency of HDACs 1, 2, 3, 6, 8, and 10. Each of these HDACs demonstrated a pHi dependence for the maximal rate of deacetylation reactions. In addition, the pH profiles for HDAC isozymes maximum catalytic efficiency "were bell-shaped, with maxima in the range of pH 7.6-8.3" (Shultz et al., 2004). Flash photolysis of NBA as described herein is capable of inducing discrete reductions in pHi that could be maintained for prolonged periods of time (FIGS. 15-16). Lowering the pHi moves the catalytic rate away from the maximum catalytic efficiency; significant reductions in pHi may serve as a novel inhibitor of HDACs and reductions in the pathogenesis of a myriad of diseases implicated with over activity of HDACs.

G. Stem Cell Pluripotency

Stem cells are a highly studied area of biology; however, the process to create stem cells yields very few viable dedifferentiated cells. Current techniques aim to reprogram terminally differentiated cells by reverting them back, or dedifferentiating, into an embryonic state. Many cells in the body remain in a controlled dividing state and are commonly located in regions of the body that are in need of constant source of cell replacement or cell division, such as skin cells and bone marrow cells. Gao et al., (*Cellular Physiology and Biochemistry*, 2014, 33(1):185-94) recently reported that human-derived mesenchymal umbilical cord cells (hUC-MSCs) differentiated into osteoblast cells in response to sustained decreases in $pH_i$ alone. Gao et al., (*Cellular Physiology and Biochemistry*, 2014, 33(1):185-94) optically measured $pH_i$ while inducing decreases in $pH_i$ by exposing the hUC-MSCs to the ammonium chloride prepulse technique, while simultaneously blocking NHE1 with cariporide. The methods described herein allow the induction of precise, incremental decreases in only $pH_i$ for longer, sustained intervals to achieve differentiation from certain stem cell lines (Gao et al., *Cellular Physiology and Biochemistry*, 2014, 33(1):185-94).

H. Neuronal Activities

Protein structure and function can be altered by ionization by free $H^+$. Several studies support the important role of pH on proteins involved in central nervous system signaling. Acid-activated currents described in hippocampal neurons by Wemmie et al., (Neuron, 2002, 34(3):463-77), were necessary for long-term potentiation, as the loss of these acid sensing ion channels (ASIC) in null mice resulted in impaired hippocampal long-term potentiation and defective eyeblink conditioning and spatial learning. The ASIC 1a serves as a proton receptor on dendritic spines of hippocampal neurons and influences intracellular calcium signaling (Zha et al., Proc Natl Acad Sci USA, 2006, 103(44):16556-61). Increases in the concentration of extracellular free $H^+$ affects many ligand gated ion channels; acetylcholine and NMDA receptors are inhibited by acidic extracellular pH and inhibited by alkaline extracellular pH (Del Castillo et al., 1962, J. Cell Comp Physiol 59:35-44; Giffard et al., Brain Res, 1990, 506:339-42; Palma et al., 1991, J Membr Biol, 120:67-73; Traynelis and Cull-Candy, 1990, Nature, 345:347-50). GABA receptor activities are enhanced by acidic extracellular pH and inhibited by alkaline extracellular pH (Kaila and Ransom, 1994, pH and brain function (New York: Wiley-Liss); Smart and Constanti, 1982, Proc R Soc Lond B Biol Sci, 215:327-41; Takeuchi and Takeuchi, 1967, J Physiol, 1967, 191:575-90. The ability of our technique to cause focal acidosis in the extracellular space adjacent to the above listed ligand-gated ion channels, and virtually all ligand-gated ion channels that are affected by protonation, will provide a unique mechanism to alter neuronal input and functional output of neural circuits.

III. Targeting Agents

Targeting agents can be attached to the compounds or particles described herein to guide or target the conjugates to the target area in vivo. The targeted delivery in vivo enhances the cellular uptake of these compounds or particles to enhance therapeutic efficacies. In certain aspects, antibodies or cell penetrating peptides can be for targeted delivery to the tumor site.

In one aspect of the invention, the targeting moiety is a single chain antibody (SCA) or single-chain antigen-binding antibody, monoclonal antibody, cell adhesion peptides such as RGD peptides and Selectin, cell penetrating peptides (CPPs) such as TAT, Penetratin and (Arg)9, receptor ligands, targeting carbohydrate molecules or lectins, oligonucleotide, oligonucleotide derivatives such as locked nucleic acid (LNA) and aptamers, or the like.

The targeting moieties can be labeled such as biotinylated compounds, fluorescent compounds, radiolabelled compounds. A suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging or detection during administration, treatment, and so forth. Optionally, the diagnostic tag is incorporated into and/or linked to a conjugated photo-activated moiety, allowing for monitoring of the distribution of a therapeutic biologically active material within an animal or human patient.

The terms "single chain antibody" (SCA), "single-chain antigen-binding molecule or antibody" or "single-chain Fv" (sFv) are used interchangeably. The single chain antibody has binding affinity for the antigen. Single chain antibody (SCA) or single-chain Fvs can and have been constructed in several ways. A description of the theory and production of single-chain antigen-binding proteins is found in commonly assigned U.S. patent application Ser. No. 10/915,069 and U.S. Pat. No. 6,824,782, the contents of each of which are incorporated by reference herein.

IV. Permanent and Releasable Linkers

Linkers used in context of the current invention can include bifunctional linkers. The bifunctional can be permanent or releasable linkers. The bifunctional linkers include amino acids, amino acid derivatives, or chemical linkers. Amino acids can be among naturally occurring and non-naturally occurring amino acids. Derivatives and analogs of the naturally occurring amino acids, as well as various art-known non-naturally occurring amino acids (D or L), hydrophobic or non-hydrophobic, are also contemplated to be within the scope of the invention. A suitable non-limiting list of the non-naturally occurring amino acids includes 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-aminobutyric acid, desmosine, 2,2-diaminopimelic acid, 2,3-diaminopropionic acid, N-ethylglycine, N-ethylasparagine, 3-hydroxyproline, 4-hydroxyproline, isodesmosine, allo-isoleucine, N-methylglycine, sarcosine, N-methyl-isoleucine, 6-N-methyl-lysine, N-methylvaline, norvaline, norleucine, and ornithine. Some preferred amino acid residues are selected from glycine, alanine, methionine and sarcosine, and more preferably, glycine.

A. Releasable Linkers

In certain aspects the compounds or particles described herein contain a photo-activated moiety attached to a releasable linker. The photo-activated moiety can be released in a controlled manner.

Among the releasable linkers can be benzyl elimination-based linkers, trialkyl lock-based linkers (or trialkyl lock lactonization based), bicine-based linkers, acid labile linkers, lysosomally cleavable peptides and capthepsin B cleavable peptides. Among the acid labile linkers can be disulfide bond, hydrazone-containing linkers and thiopropionate-containing linkers.

Alternatively, the releasable linkers are intracellular labile linkers, extracellular linkers and acidic labile linkers. The acidic labile linkers, such as hydrazone linkages, can be hydrolyzed in the acidic lysosome environment. Some suitable releasable linkers are oligopeptides including such as Val-Cit, Ala-Leu-Ala-Leu (SEQ ID NO. 1), Gly-Phe-Leu-Gly (SEQ ID NO. 2) and Phe-Lys. One preferred releasable linker is a peptidyl linker (Val-Cit) which can be specifically degraded by capthesin B.

Various releasable linkers, benzyl elimination based or trialkyl lock based, are described, for example, in commonly assigned U.S. Pat. Nos. 6,180,095, 6,720,306, 5,965,119, 6,624,142 and 6,303,569, the contents of each of which are incorporated herein by reference. The bicine-based linkers are also described in commonly assigned U.S. Pat. Nos. 7,122,189 and 7,087,229 and U.S. patent application Ser. Nos. 10/557,522, 11/502,108, and 11/011,818, the contents of each of which are incorporated herein by reference.

B. Permanent Linkers

In certain aspects, the targeting moiety such as the SCA is attached to the multifunctional linker through a permanent linker. The permanent linkers are capable of conjugating the targeting moiety and the multifunctional linker. One preferred permanent linker can be a molecule like a maleimidyl-containing molecule which can provide a thio-ether bond.

C. Pharmaceutical Formulations and Administration

In certain embodiments, compositions comprise 1, 2, 3 or more therapeutic agents with one or more of the following: a pharmaceutically acceptable diluent; a carrier; a solubilizer; an emulsifier; a preservative; and/or an adjuvant. Such compositions may contain an effective amount of at least one anti-cancer agent. Thus, the use of one or more anti-cancer agents that are provided herein in the preparation of a pharmaceutical composition of a medicament is also included. Such compositions can be used in the treatment of a variety of cancers or other diseases or conditions.

The agents described herein may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the therapeutics agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor is also contemplated by the present invention. When administering the compositions by injection, the administration may be by continuous infusion or by single or multiple boluses. For parenteral administration, the therapeutic agents may be administered in a pyrogen-free, parenterally acceptable aqueous solution comprising the desired anti-cancer agents in a pharmaceutically acceptable vehicle. A particularly suitable vehicle for parenteral injection is sterile distilled water in which one or more therapeutic agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight. Therapeutic compositions or regimens may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, the target tissue or cell is a cancer or cancer cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, intracranially, regionally, percutaneously, topically, intrarterially, intravesically, or subcutaneously.

Methods of treating cancer or other diseases or conditions may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. In addition, a cell or patient may be administered a protease or peptidase to increase the production of infectious EEV form of the virus from cells. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials. Dulbecco's modified Eagle's medium (DMEM), RPMI 1640 (Roswell Park Memorial Institute 1640), fetal bovine serum (FBS), horse serum, gentamicin, trypsin-EDTA, Carboxy-DCFDA (5-(and-6)-Carboxy-2',7'-Dichlorofluorescein Diacetate) and Annexin V Alexa Fluor 568 were bought from Life Technologies. NaCl, KCl, MgCl2, CaCl2, HEPES, and glucose were all purchased from Fisher Scientific. 2-Nitrobenzaldehyde (NBA), Amiloride, Nigericin, NGF-7S, Corning® 75 cm$^2$ Rectangular Canted Neck Cell Culture Flask with Vent Cap were all purchased from Sigma Aldrich. Rat pheochromocytoma (PC12) cells and human breast adenocarcinoma (MCF-7) cells were purchased from the American Type Culture Collection. Thirty-five mm culture dishes were purchased from Santa Cruz Biotechnology. Nanoparticles were synthesized by Dr. Brian Yust and Francisco Pedraza of the University of Texas at San Antonio. Cells and Cell Culture PC12 cells were cultured in RPMI 1640 (1×) supplemented with 5% FBS, 10% Horse Serum and 500 µL of gentamicin at 37° C. under an atmosphere of 5% $CO_2$ and 95% air. The cells were plated on 35 mm dishes at an appropriate range and cultured until 80-90% confluent. MCF-7 cells were cultured in DMEM (1×) supplemented with 5% FBS and 500 µL of gentamicin at 37° C. under an atmosphere of 5% $CO_2$ and 95% air. The cells were plated in a 75 $cm^2$ Corning flask allowing for cell growth to appropriate density and passed to 35 mm dishes, then grown until 80-90% confluent for experimentation. When PC12 or MCF-7 cells were passed, 1 mL of 0.25% Trypsin-EDTA (1×) was used to suspend cells for passage. DCFDA Stock Solution Carboxy-DCFDA (5-(and-6)-Carboxy-2',7'-Dichlorofluorescein Diacetate; 1 mg) was dissolved in 201 µL of dimethyl sulfoxide (DMSO) to create a stock solution of 9.4 mM. The stock solution was stored in a dark biosafety cabinet to protect the light sensitive compound.

Calibrating and Measuring pH with DCFDA. For ratiometric pH, measurements, PC12 cells were loaded with the pH-sensitive dye Carboxy-DCFDA (10 µM in rat aCSF). Nigericin was titrated to a pH of 2.0, 4.0, 5.0, 6.0, 7.0 or 8.0. The emitted fluorescence of DCFDA was recorded from cells at each of the titrated pH solutions. The ratiometric emitted fluorescence intensity was observed at an excitation of 495 nm/440 nm on 30 second intervals until emitted fluorescence (504/530 nm) reach a steady state. Each ratio from individual cells (n=421) was recorded for each pH. A curve of best fit was created ($R^2$=93.02) and used for the conversion of fluorescence to $pH_i$.

NBA Loading. NBA was (3.0224 grams) dissolved in 500 mL of methanol to make a stock solution of 40 mM. For each experiment, 75 µL of stock was combined with 3 mL of rat aCSF for cell bath application. The final dilution of 1 mM NBA-rat aCSF is well below the allowable 5 mM limit of cytotoxicity (Sweitach et al., *Biophys J*, 2007, 92(2):641-53). The NBA loading procedure for PC12 cells was the same procedure for the MCF-7 cells.

Apoptosis Indicator. The apoptosis indicator Annexin V Alexa Fluor 568 was stored in a solution containing 25 mM HEPES, 140 mM NaCl, 1 mM EDTA, pH 7.4, plus 0.1% bovine serum albumin (BSA). A 10 µL of stock Annexin V Alexa Fluor 568 was diluted in 2 mL of binding buffer. The binding buffer consisted of: 10 mM HEPES, 140 mM NaCl, and 2.5 mM CaCl2, at a pH of 7.4.

Amiloride Procedure. Amiloride (N-Amidino-3,5-di-amino-6-chloropyrazinecarboxamide hydrochloride hydrate) (266.09 mg) was added to 20 mL of DMSO to make a final stock solution of 50 mM. This stock was further diluted to 1 mM prior to bath application to cultured cells.

Rat aCSF stock solution. PC12 and MCF-7 cells were perfused in 2 mL of rat aCSF solution (150 mM NaCl, 5 mM KCl, 1 mM MgCl2, 5 mM HEPES, 5 mM glucose, pH 7.4) during experimental procedure.

Optic Recording of $pH_i$ PC12. DCFDA stock solution was diluted to a concentration of 10 µM in a 3 mL rat aCSF solution. PC12 cells were flashed every 30 second at 495/440 nm for a duration of 900/700 ms, respectively, at 40× magnification and 2 seconds at each wavelength under the 10× magnification. Cells were washed three times with rat aCSF after 10 minutes and prior to recording fluorescence to monitor steady state.

Optical Recording of pH, MCF-7. DCFDA stock solution was diluted to a concentration of 10 µM in a 3 mL rat aCSF solution. MCF-7 cells were flashed every 30 seconds at 495/440 nm for a duration of 900/700 ms, respectively, at 40× magnification and 2 seconds at each wavelength under the 10× magnification. Cells were washed three times with rat aCSF after a steady state of fluorescence was observed, indicating that the fluorescence reached its max fluorescence since cancer cells are more alkaline. Optical recording of $pH_i$ was monitored for a minimum of 10 minutes to represent a steady state.

Optical Recording of pHi MDA-MB-231. DCFDA stock solution was diluted to a concentration of 10 µM in a 3 mL rat aCSF solution. MBA-MD-231 cells were flashed every 30 seconds at 495/440 nm for a duration of 900/700 ms, respectively, at 40× magnification and 2 seconds at each wavelength under the 10× magnification. Cells were washed three times with rat aCSF after a steady state of fluorescence was observed, indicating that the fluorescence reached its max fluorescence since cancer cells are more alkaline. Optical recording of $pH_i$ was monitored for a minimum of 10 minutes to represent a steady state.

NBA Loading for Focal Acidification of PC12. Seventy-five µL of NBA stock solution was mixed in 3 mL of rat aCSF and bath applied to PC12 cells for 10 minutes. After bath application, cells were washed a minimum of three times with rat aCSF. PC12 cells were exposed to UV light using various flash paradigms. After each exposure, pH was monitored for 2 minutes to quantify $pH_i$ acidification.

NBA Load for Focal Acidification of MCF-7. Seventy-five µL of NBA stock solution was mixed in 3 mL of rat aCSF and bath applied to MCF-7 cells for 10 minutes. After bath application, cells were washed a minimum of three times with rat aCSF. MCF-7 cells were exposed to 60-30-60 UV light paradigm. After each exposure, pH was monitored for 2 minutes to quantify $pH_i$ acidification.

NBA Load for Focal Acidification of MDA-MB231. Seventy-five µL of NBA stock solution was mixed in 3 mL of rat aCSF and bath applied to MDA-MB-231 cells for 10 minutes. After bath application, cells were washed a minimum of three times with rat aCSF. MDA-MB-231 cells were exposed to 60-30-60 UV light paradigm. After each exposure, pH was monitored for 2 minutes to quantify $pH_i$ acidification.

Cell Death Quantification PC12. One hour after the UV flash paradigm to induce intracellular acidosis, the cells were lightly washed and the media was replaced with the phosphatidylserine indicator Annexin V Alexa Fluor 568. This solution was made using 10 µL of the stock solution and diluted in 2 ml of rat aCSF. Fifteen minutes was allowed for membrane binding, then fluorescence was monitored for the next hour or until all cells were expressing apoptosis.

Cell Death Quantification MCF-7. After UV flash paradigm, the presences of blebs were observed and recordings of the pH in the intrablebular inflationary space ($pH_b$) were acquired using the DCFDA fluorescence as they expanded. The blebs seen with DCFDA fluorescence showed continuous expansion and never reduced in size. We quantified blebs as cellular death based on previously published findings which described blebbing as an irreversible death process (Andrade et al., *Biology of the Cell*, 2010, 102(1):25-35).

Cell Death Quantification MDA-MB-231. One hour after the UV flash paradigm to induce intracellular acidosis, the cells were lightly washed and the media was replaced with the phosphatidylserine indicator Annexin V Alexa Fluor 568. This solution was made using 10 μL of the stock solution and diluted in 2 ml of rat aCSF. Fifteen minutes was allowed for membrane binding, then fluorescence was monitored for the next hour or until all cells were expressing apoptosis. As with MCF-7 cells, we quantified blebs as cellular death based on previously published findings which described blebbing as an irreversible death process (Andrade et al., *Biology of the Cell,* 2010, 102(1):25-35).

Amiloride Application. The NHE1 blocker, Amiloride, was bath applied at a pH of 7.4 to MCF-7 cells at concentrations ranging from 1 μM to 1 mM. After the cells were loaded with DCFDA, NBA, respectively washed, and exposed to the UV paradigm, $pH_b$ was recorded.

Nanoparticle Application. Nanoparticles of various rare earth doped upconverting cores coated with various hydrophilic biocompatible polymer, such as polyethylene glycol (PEG), cell membrane mediated polymers were synthesized and introduced to MCF-7 cancer cells. The two particles tested consisted of $KYb_2F_7$ or $NaYF_4$. These cancer cells were incubated in growth media with nanoparticles ranging from 10 minutes to one week. When preparing for experimentation, the cancer cells were washed with rat aCSF five times and placed under the microscope, then loaded with DCFDA under the same procedure as previously mentioned. A continuous wave of 980 nm diode laser was aligned to the region of cells recording $pH_i$ and set to 400 or 700 mW. The laser shutter was manually controlled for exposure of 10 or 20 minutes.

Control Experiments. Controls in each experiment were performed by moving 10 mm or more away from the UV or 980 nm exposed region. Recordings of $pH_i$ were performed to detect if NBA or the nanoparticle affected the cell or inadvertently uncaged hydrogens in the periphery of the plate. Detection of apoptosis and/or blebs was performed using Annexin V Alexa Fluor 568 and DCFDA optical recording. Control experiments were performed in the following conditions: UV alone, time alone, and NBA alone. Each one of the control experiments was performed for a minimum of 3 hours.

Results

Figure 3A:
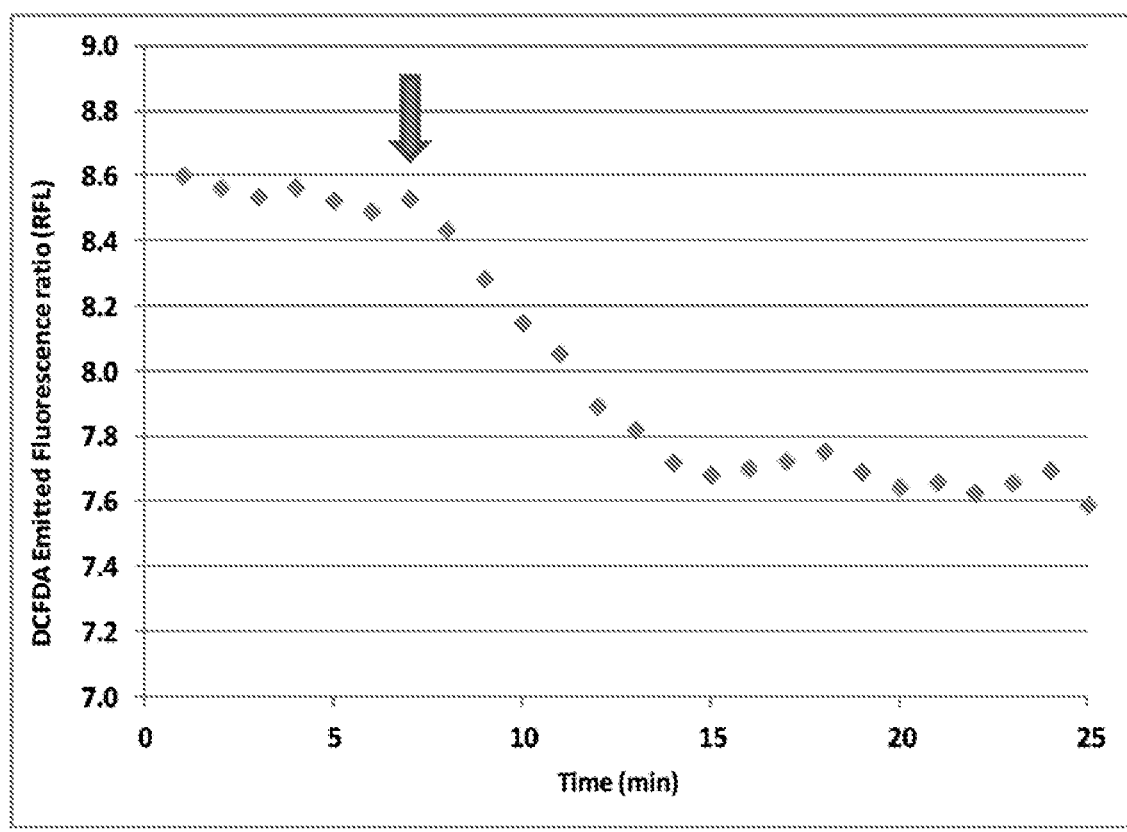
FIG. 3 illustrates the ratio of DCFDA fluorescence ($R_{FL}$) of PC12 cells in response to bath application of high potassium/nigericin solutions titrated to pH values of 2.0, 4.0, 5.0, 6.0, 7.0, and 8.0. This DCFDA calibration curve permits the optical conversion of DCFDA emitted fluorescence ratios to intracellular pH.

DCFDA Calibration. The emitted fluorescence of cells exposed to pH specific-nigericin solution was used for the construction of the DCFDA calibration curve. Ratiometric fluorescence of individual cells was recorded at pH of 2.0, 4.0, 5.0, 6.0, 7.0, or 8.0. Each pH unit represents a separate experiment at which several cells were optically recorded and monitored for a steady state when exposed to the pH specific-nigericin solution (FIG. 3a). Data were graphed and revealed a line of best fit with an R-squared value (y=−0.1356x2+2.62x−3.6204) ($R^2$=0.93), permitting the future conversion of emitted fluorescence to $pH_i$. After the calibration was completed, the formula applied to each experiment showed the average starting $pH_i$ was 7.7.

Induced Acidosis in PC12 Cells. We assessed the ability of photoactivated NBA to focally induce significant intracellular acidosis by optically recording pH, from individual PC12 cells in vitro (n=423) prior to and after proton release from NBA. After loading with DCFDA, emitted fluorescence ratios were recorded before exposing the cells to varying flash-time paradigms of 350 nm wavelength UV light. Mean pH, of the PC12 cells after application of NBA and prior to photolysis (7.55±0.025) was significantly different from mean pH, after photolysis of NBA with UV exposure (6.37±0.03; P<0.001). Changes in pH, ($\Delta\ pH_i$) with treatment were normalized as a change from $pH_i$ prior to treatment ($\Delta\ pH_i$=1.18).

Quantification of PC12 Cell Death. After focal acidification was achieved in PC12 cells, Annexin V Alexa Fluor 568 was bath applied to mark for phosphatidylserine membrane inversion resulting from and indicative of apoptosis. The cells were monitored for at least an hour after flash photolysis in the presence of NBA for fluorescence which would indicate apoptosis. We observed a range of apoptosis spanning from 76 to 100% (n=362; R2=0.98) with an average apoptosis of 84.0±1.33%. Linear regression analysis of these data over time indicated significant apoptosis was achieved within 2 hours in response to acidosis from the flash photolysis of NBA (P<0.01). The mean percent apoptosis with NBA treatment (84.0±1.33%) was significantly greater from control experiments in which PC12 cells were exposed to UV light in the absence of NBA (n=76; R2=−0.54; P<0.001). The percentage of cells exhibiting apoptosis in response to UV exposure alone ranged from 2.3 to 10.3%, with a mean percentage of 6.4±1.0%. The percentage of apoptosis with NBA and UV treatment was also significantly greater (P<0.01) than control experiments in which cells were exposed to neither NBA nor UV light (i.e. the effects of time alone; n=71; R2=0.92). The percentage of cells exhibiting apoptosis in response to time alone ranged from 3.1 to 4.5%, with a mean percentage of 3.8±0.4%. The percentage of cells exhibiting apoptosis in response to NBA alone was 2.1% (n=47). Linear regression analyses indicated that the percentage of apoptosis in response to UV exposure alone, time alone, or NBA alone were significantly less than the percentage of apoptosis in response to NBA and UV treatment (P<0.01). Control experiments were not significantly different from each other (P<0.01).

Induced Acidosis in MCF-7 Cells. After assessing the ability of NBA to focally decrease the pH, in PC12 cells, the same experimental procedure was performed on an MCF-7 breast cancer cells. Emitted fluorescence ratios were taken before and after NBA flash photolysis to monitor $pH_i$. Mean $pH_i$ of MCF-7 cells after the cells after loading with NBA and before the 60-30-60 UV flash paradigm (7.38±0.13; n=76) was significantly different from the mean $pH_i$ of cells after the flash paradigm in the presence of NBA (6.22±0.15). Changes in $pH_i$ with treatment were normalized as a change from $pH_i$ prior to treatment. The post treatment mean $\Delta\ pH_i$ (1.16 pH units) was significantly different from the mean $pH_i$ prior to treatment (P<0.001).

Quantification of MCF-7 Cell Death. After focal acidification was achieved in MCF-7 cells, Annexin V Alexa Fluor 568 was bath applied to mark for phosphatidylserine membrane inversion resulting from and indicative of apoptosis. The cells were monitored for at least 1 hour after flash photolysis in the presence of NBA for fluorescence which would indicate apoptosis. MCF-7 cells were also observed to exhibit cellular blebbing upon focal intracellular acidification and did not exhibit fluorescence in the presence of Annexin V Alexa Fluor 568 until the bleb completely separated from the cell or after several hours (1-6 hrs) post treatment. As previously discussed, research indicated that blebbing was indicative of apoptosis. The number of blebs were counted upon formation as a function of time as another indication of cell death. While previous research indicates that upon activation of NCX1 there is often a reduction in the size of the bleb (Yi et al., 2012), we did not observe any reductions in the occurrence or size of blebs over time in response to our NBA-UV treatment. In response to flash photolysis of NBA, we observed a range of apoptosis, as indicated by cellular blebbing and/or apoptosis via fluorescence of Annexin V, spanning from 94.9 to 100.0% (n=262; R2=0.92) with an average apoptosis over time of 98.3±0.3%. Linear regression analysis revealed a significant decrease (P<0.01) the percentage of apoptosis for MCF-7 cells exposed to only UV light (7.1%) over 2 hours. The percentage of apoptosis observed in MCF-7 cells exposed only to NBA (2.3%, n=236, R2=0.87) was significantly less (P<0.0001) than the percentage of apoptosis in MCF-7 cell treated with NBA and UV light. Our control experiment to evaluate the percentage of apoptosis in response to time alone (n=20) revealed no apoptosis over 2 hours. As our results produced no cell death what so ever, linear regression was not performed.

Induced Acidosis in MDA-MB-231 Cells. After assessing the ability of NBA to focally decrease the $pH_i$ in both PC12 and MCF-7 cells, the same experimental procedure was performed on the highly aggressive, triple negative MDA-MB-231 breast cancer cells. Emitted fluorescence ratios were taken before and after NBA flash photolysis to monitor $pH_i$. Mean $pH_i$ of MDA-MB-231 cells after the cells after loading with NBA and before the 60-30-60 UV flash paradigm (6.47±0.06; n=38) was significantly different (P<0.001) from the mean $pH_i$ of cells after the flash paradigm in the presence of NBA (2.78±0.23). The post treatment mean Δ $pH_i$ (3.68±0.18 pH units) was significantly different from the mean $pH_i$ prior to treatment (P<0.001).

Figures 18A, 18B, 18C, 18D:
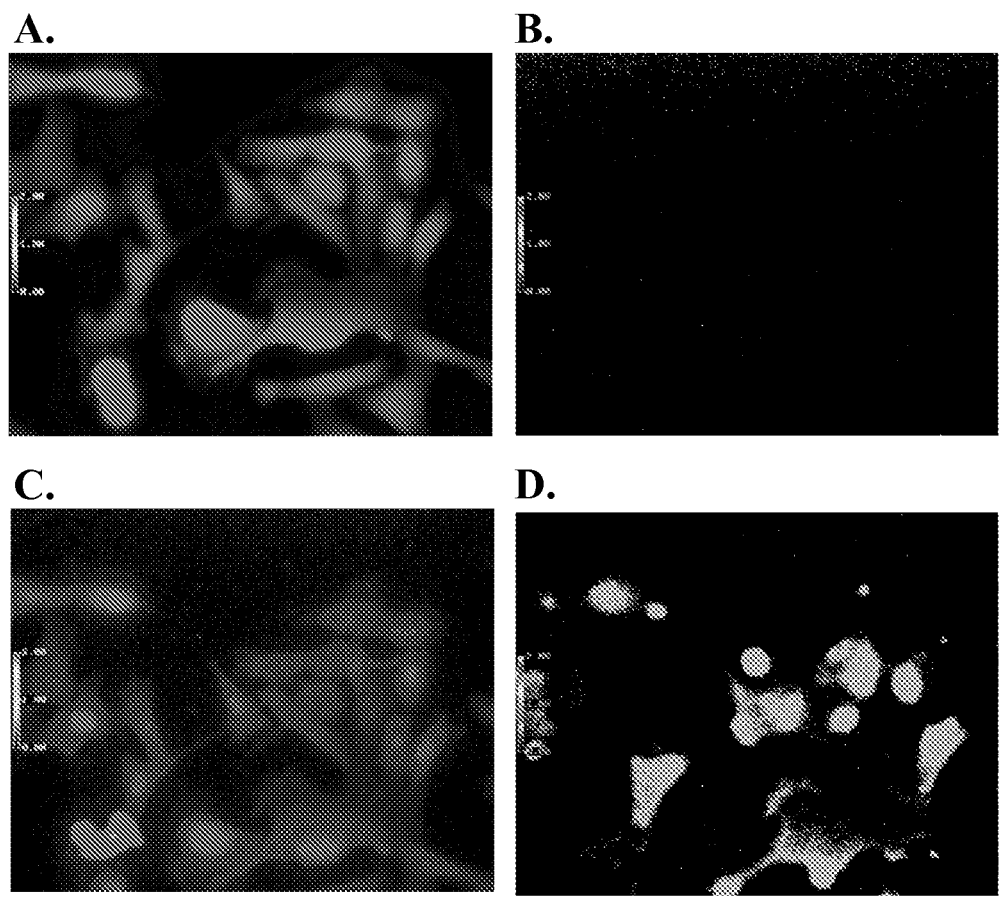
FIG. 18 illustrates MDA-MB-231 breast cancer cells in response to excitation of the pH sensitive fluorophore DCFDA (A) and the apoptotic marker, Annexin-V (B) prior to photoactivation of NBA (magnification=40×). One hour after NBA photoactivation, these same cells demonstrated a lower DCFDA emitted fluorescence (C), which coincides with a lower pHi, and significant expression of apoptosis (D). (images C & D magnification=40×).

Quantification of MDA-MB-231 Cell Death. After focal acidification was achieved in MDA-MB-231 cells, Annexin V Alexa Fluor 568 was bath applied to mark for phosphatidylserine membrane inversion resulting from and indicative of apoptosis. The cells were monitored for at least 1 hour after flash photolysis in the presence of NBA for fluorescence which would indicate apoptosis. MDA-MB-231 cells were also observed to exhibit cellular blebbing upon focal intracellular acidification and did not exhibit fluorescence in the presence of Annexin V Alexa Fluor 568 until the bleb completely separated from the cell or after several hours (1-6 hrs) post treatment. As previously discussed, research indicated that blebbing was indicative of apoptosis. Similar to our MCF-7 results, MBA-MB-231 cells demonstrated a range of apoptosis, as indicated by cellular blebbing and/or apoptosis via fluorescence of Annexin V in response to flash photolysis of NBA (FIG. 18). We observed 55.3% MDA-MB-231 cell death in less than three hours following NBA flash photolysis.

Example 2

Figure 14A:
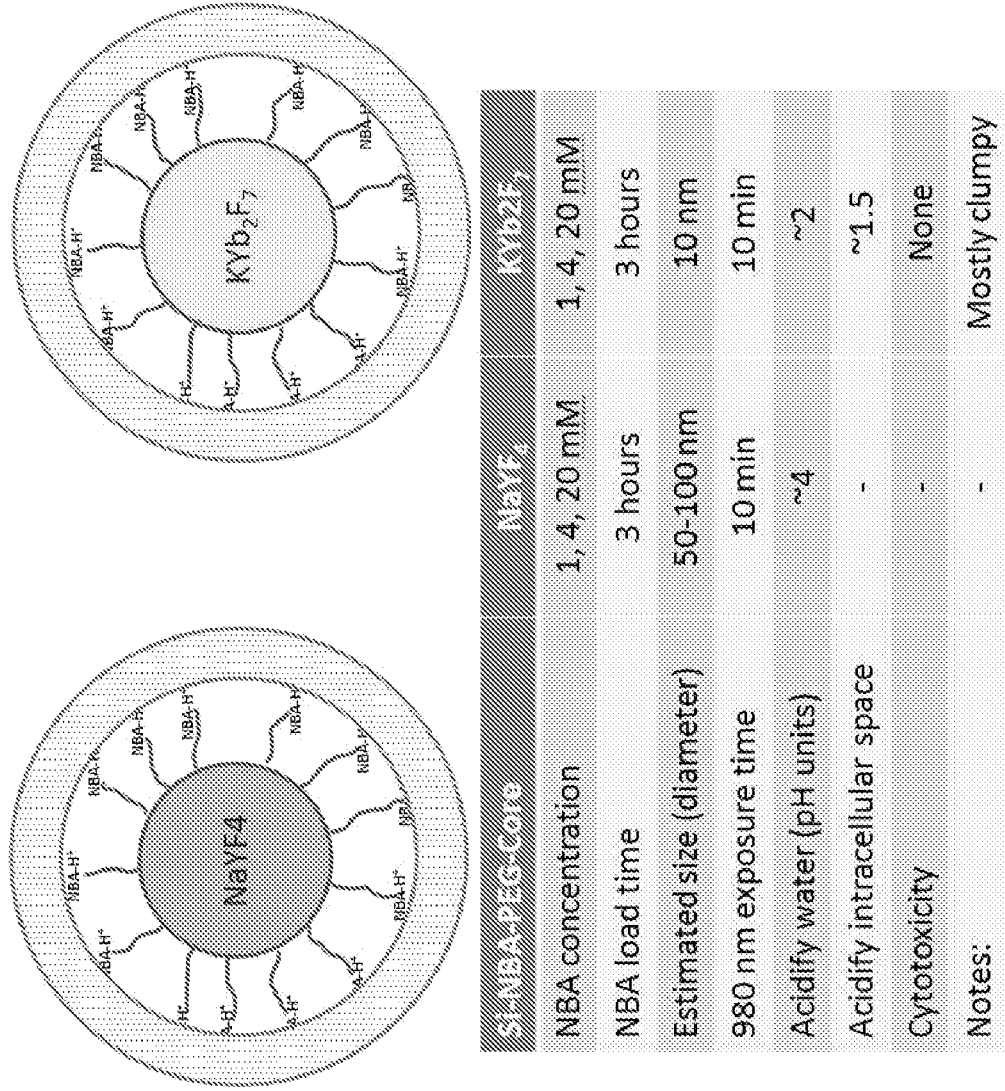
FIG. 14 illustrates a schematic representation of the KYb$_2$F$_7$ and NaYF$_4$ core nanoparticles PEGylated, doped with NBA, then coated in mesoporous-silica (A). The table in the figure contains key properties of each particle. (B) A schematic representation of the KYb$_2$F$_7$ and NaYF$_4$ core nanoparticles PEGylated then doped with NBA. The table contains key properties of each particle.
Figure 14B:
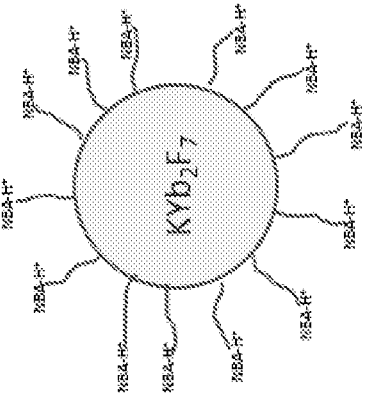
Figure 17:
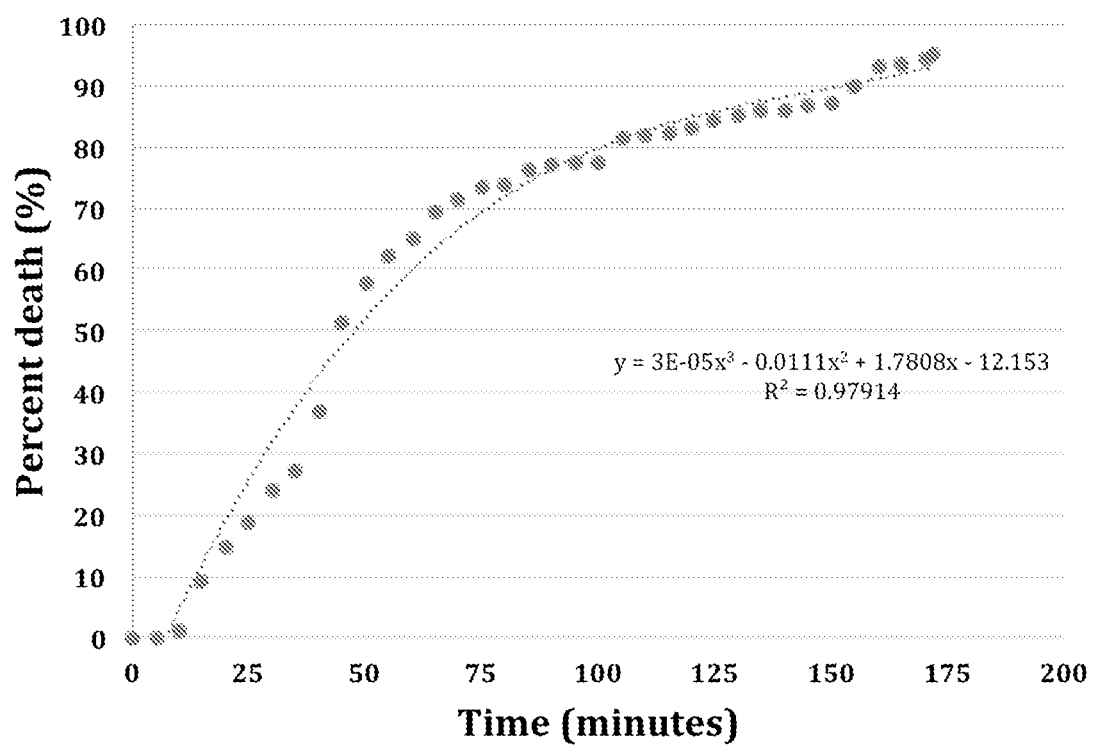
FIG. 17 illustrates the percentage of MCF-7 breast cancer cell death over time in response to the activation of a KYb$_2$F$_7$ upconverting nanoparticle in vitro. Cells were loaded with nanoparticles prior to photoactivation by 980 nm light.

Nanoparticle Induced Acidosis in MCF-7 Cell Death. Several upconversion nanoparticles were synthesized and loaded with NBA to be delivered to MCF-7 cancer cells. The nanoparticle chosen consisted of $KYb_2F_7$ core coated with PEG for NBA load (FIG. 14A). After the MCF-7 cells were loaded with DCFDA, the nanoparticles were ultrasonicated and bath applied to the cells (n=618) for 10 minutes. A 980 nm diode laser was then aligned to the cells within the field of view of the microscope. Recordings of $pH_i$ were collected for 30 minutes to monitor if the nanoparticle affected the pH or was cytotoxic; the results yielded no cytotoxicity within the timeframe. The cells were then exposed to the 980 nm wavelength for 10 minutes at 400 mW for fluorescence resonance energy transfer to NBA, well below the tolerable intensity for human cells (Idris et al., Nature Medicine, 2012, 18(10):1580-85). MCF-7 cells were then monitored for changes in $pH_i$ and for the formation of cellular blebbing indicating cell death over the next 172 minutes. After recording and application of Annexin V Alexa Fluor 568, cell death was recorded at 95.1%. Quantification of the percentage of MCF-7 breast cancer cell death in response to photo-upconversion of the $KYb_2F_7$ nanoparticle is illustrated in FIG. 17.

A second nanoparticle tested used the $KYb_2F_7$ core with a mesoporous silica coating. These nanoparticles were added to MCF-7 cells and monitored for cytotoxicity over a four day period. The cells proliferated very well and showed minimal cell death. MCF-7 cells that were exposed to the NBA nanoparticle were then loaded with DCFDA and monitored for 10 minutes. The cells were exposed to the 980 nm laser for 10 minutes at a 700 mW setting. We then recorded $pH_i$ for a 10 minute period without the laser exposure. We then exposed the MCF-7 cells to a second 10 minute 980 nm exposure. Cells were then monitored for 3 hours following the last laser excitation, recording the DCFDA fluorescence every 30 seconds. Photo upconversion of NBA using this nanoparticle resulted in 98.7% cell death (n=326) by loss in membrane integrity (Annexin V fluorescence) or blebbing. The control region in this experiment was approximately 10 mm from the laser exposed cells. MCF-7 cells in this control region were exposed to the nanoparticle for 4 days but were not exposed to the 980 nm laser. Annexin V expression or cellular blebbing indicated a 5.78% cell death (n=190) in these control cells.

Example 3

Figure 3B:
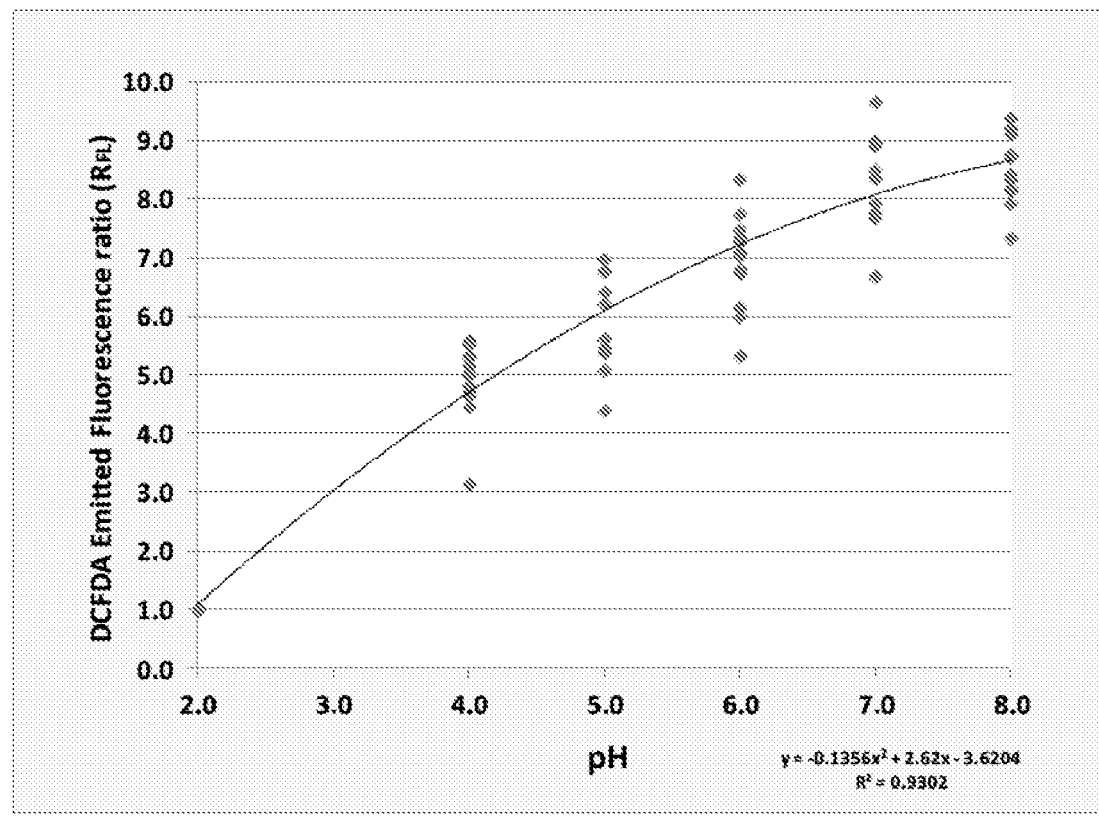
Figure 4:
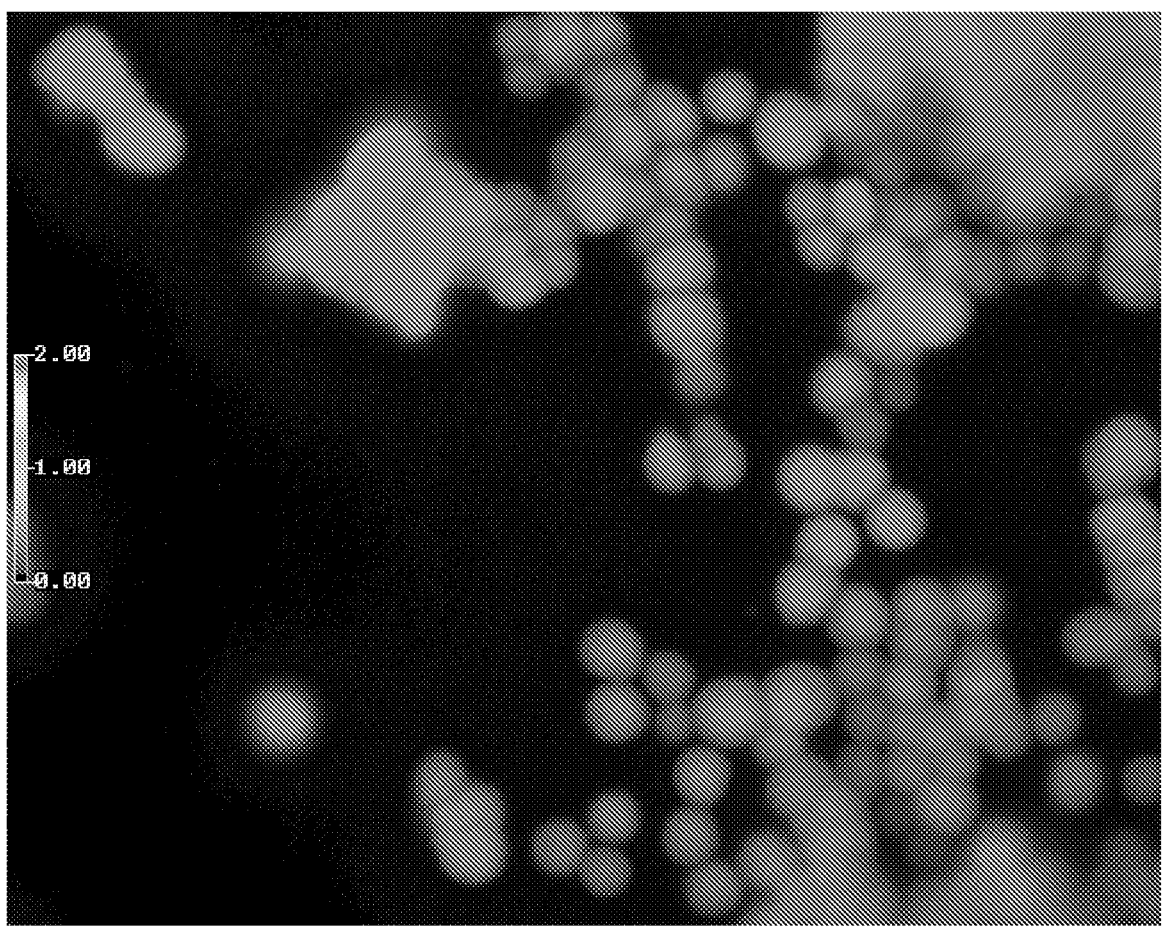
FIG. 4 illustrates the DCFDA (10 µM) emitted fluorescence of PC12 cells (40×). These cells were also loaded with NBA (1 mM).

In this embodiment of the invention, 2-nitrobenzaldehyde is used to focally induce acidosis in a system. It is necessary to prove the ability of NBA to release protons for acidification of a system, for example the intracellular space. Proof of concept experiments were performed which showed that:

We can prove, with the use of ratiometric pH-sensitive fluorescent dyes, that NBA can release a proton and induce acidosis inside of a cell. In our experiments PC12 cells were loaded with the ratiometric fluorescent dye DCFDA. DCFDA was utilized for measuring changes in the intracellular pH ($pH_i$) of a cell over a broad pH range from 2.0 to 7.0 (FIG. 3A, 3B). In this embodiment of the invention, NBA (1 mM) was bath applied at room temperature to PC12 cells and allowed to passively diffuse across the cell membrane. Emitted fluorescence ratios were taken prior to photoactivation of NBA with a flash photolysis paradigm (FIG. 15). Emitted fluorescence ratios were also recorded after NBA was exposed to a wavelength of 350 nm UV light. Using fluorescence microscopy, we can optically record and quantify changes in $pH_i$.

Figure 8:
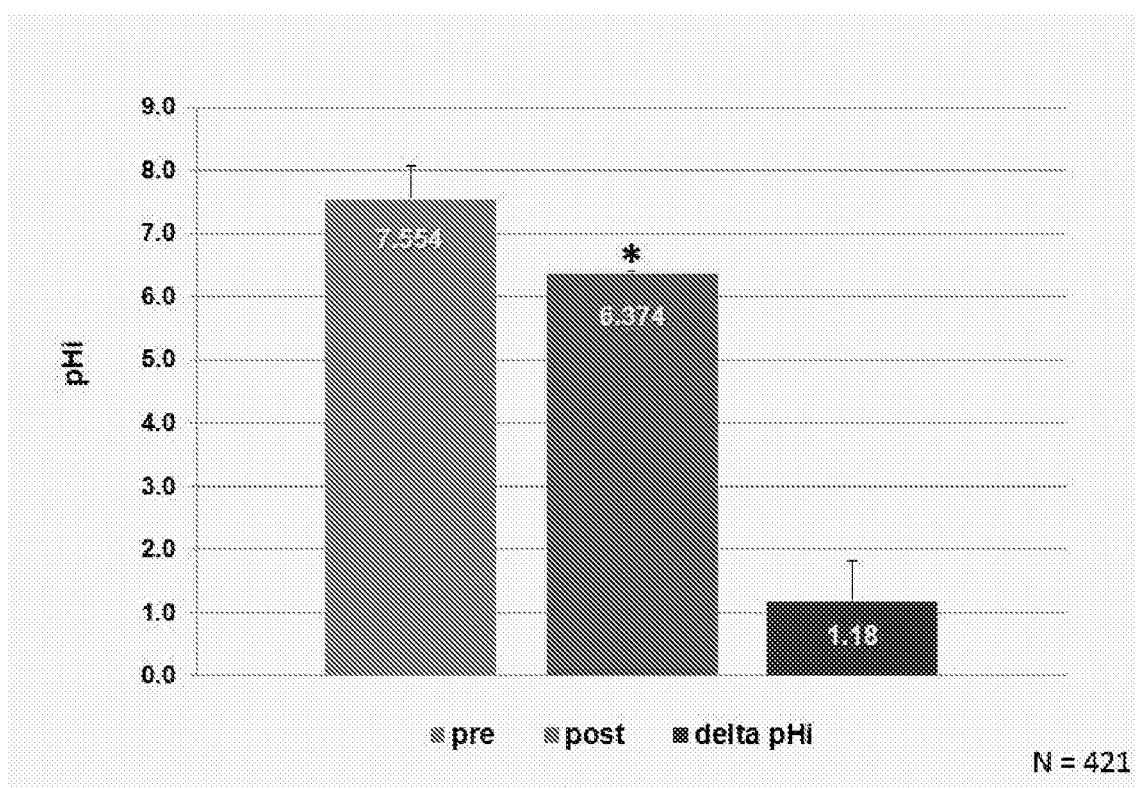
FIG. 8 illustrates mean optical recordings of pH$_i$ from PC12 cells (n=421) loaded with 10 µM DCFDA and 1 mM NBA before (7.55 pH$_i$) and after (6.37 pH$_i$) flash photolysis. We were able to induce a significant acidosis (P<0.01) in response to flash photolysis of NBA. The mean change in pH$_i$ (Δ pH$_i$) was 1.18 pH units. These data support our abilities to 1) optically record valid pH$_i$ measurements, and 2) quantify the pH$_i$ decreases associated with the uncaging of H$^+$ from NBA.
Figures 9A, 9B, 9C, 9D:
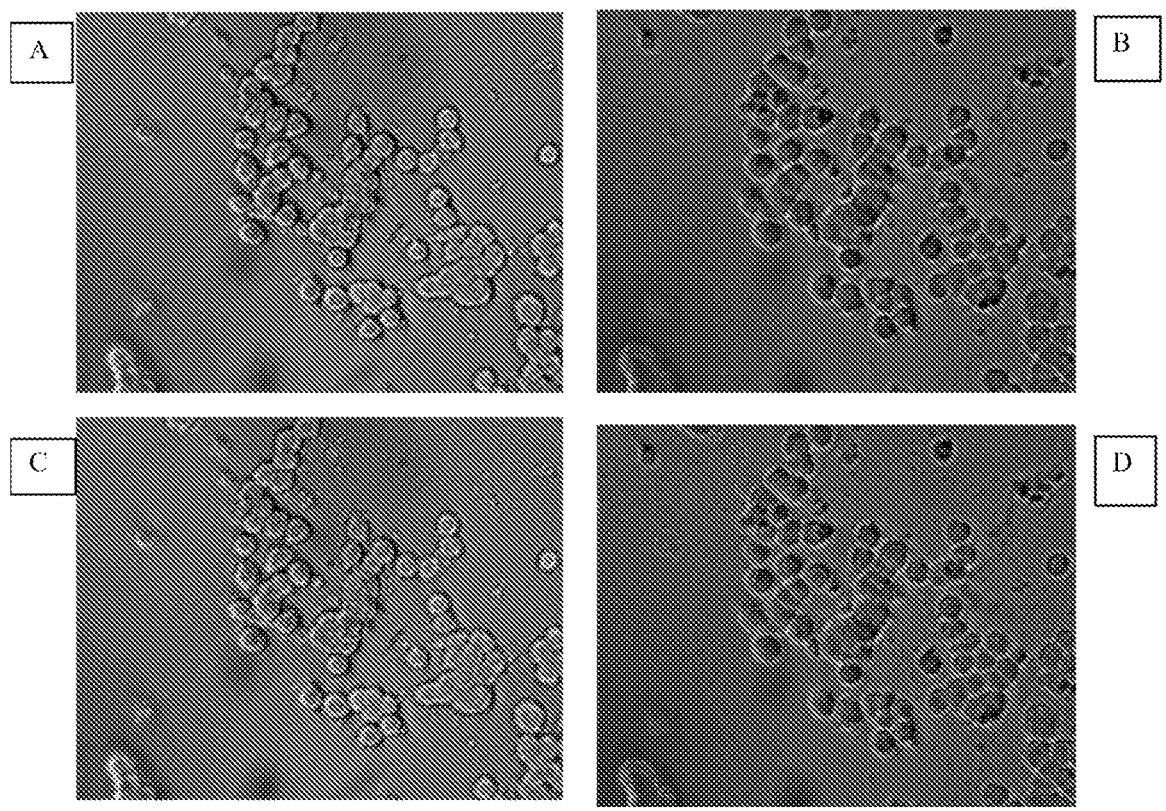
FIG. 9 illustrates representative pictures of differential interference contrast (DIC) microscopy of PC12 cells (n=68) at 40× magnification over the course of an experiment to induce acidosis with a 60-30-60 UV flash paradigm. (A) PC12 cells prior to flash photolysis. (B) PC12 cells following flash photolysis, showing reduction of cell size and changes in cell morphology. (C) PC12 cells prior to UV flash with an overlay depicting the outlines of cell shape. (D) PC12 cells following UV flash and uncaging of H$^+$, with an overlay of the pre-treatment cell outlines shown in (C). (E) A DIC image PC12 cells approximately 2 hours following flash photolysis of NBA with an overlay of the fluorescent apoptosis marker Annexin V.
Figure 9E:
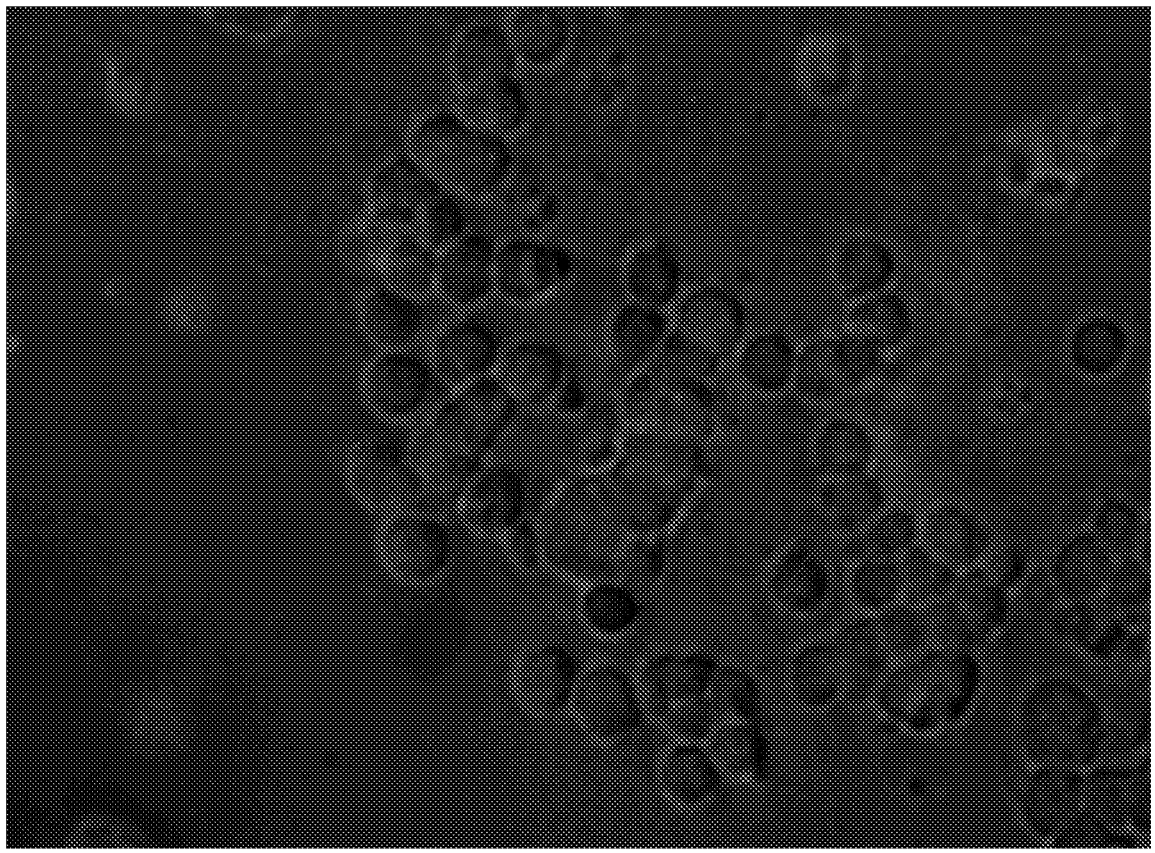
Figures 10A, 10B, 10C, 10D:
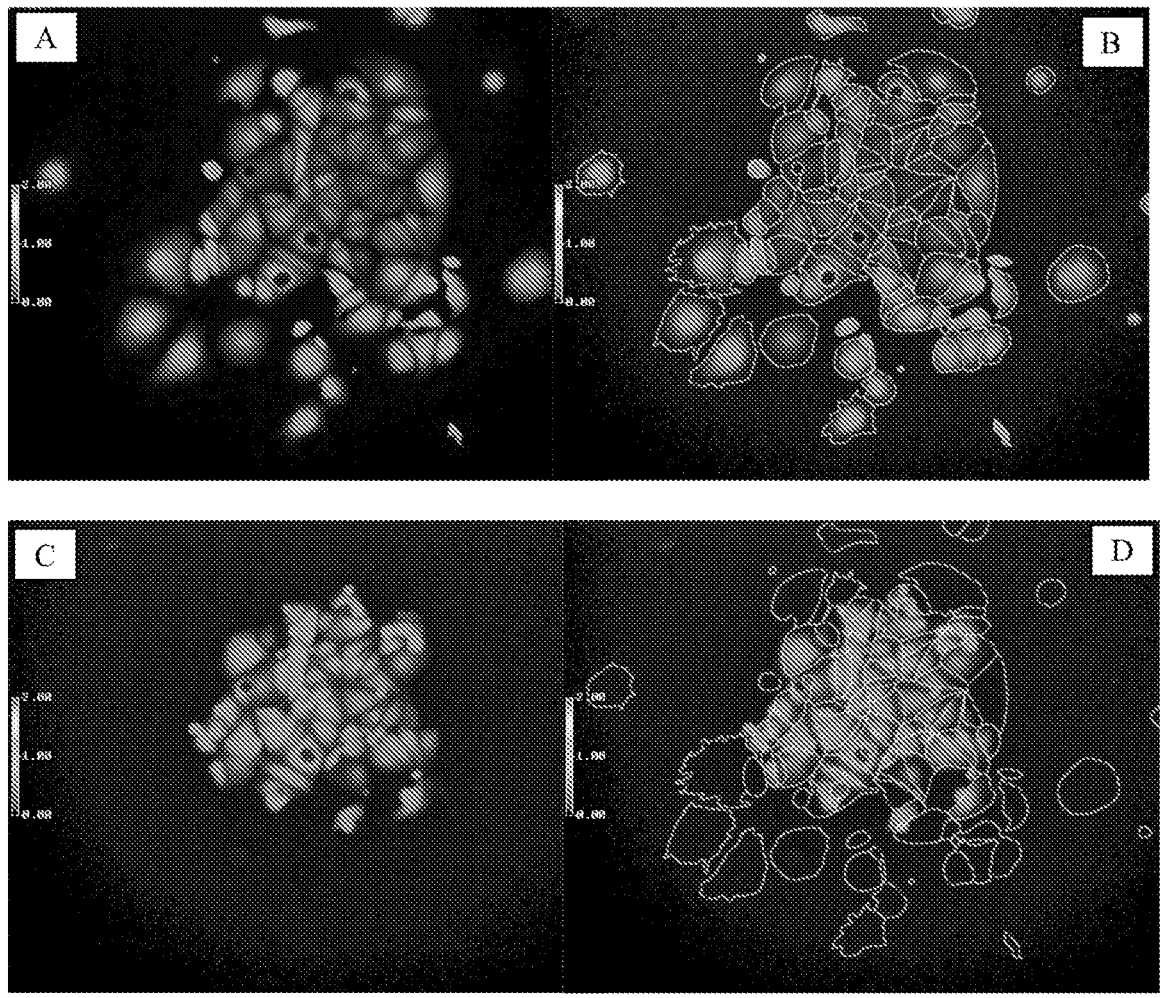
FIG. 10 illustrates representative pictures of ratiometric fluorescence microscopy of MCF-7 cells at 40× magnification over the course of an experiment to induce acidosis with a 60-30-60 UV flash paradigm. (A) MCF-7 cells loaded with the 10 µM DCFDA prior to flash photolysis. (B) MCF-7 cells following flash photolysis, showing reduction of cell size and changes in cell morphology. (C) MCF-7 cells prior to UV flash with an overlay depicting the outlines of cell shape. (D) MCF-7 cells following UV flash (t=79 min) with an overlay of the pre-treatment cell outlines shown in (C). (E) DIC of MCF-7 cells approximately 2 hours following flash photolysis of NBA. The scale bar indicates fluorescence ratio measurements below 2.00.
Figure 10E:
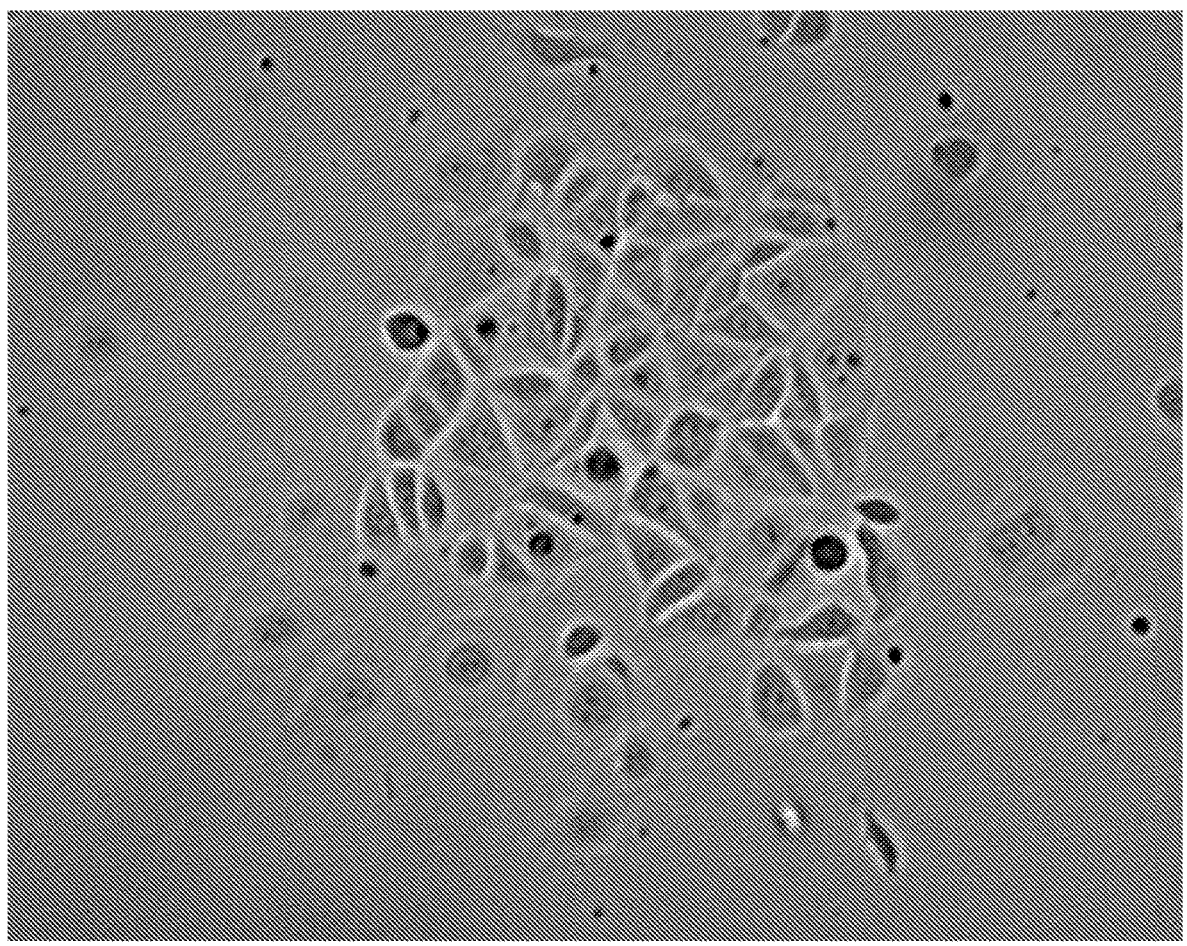
Figure 11:
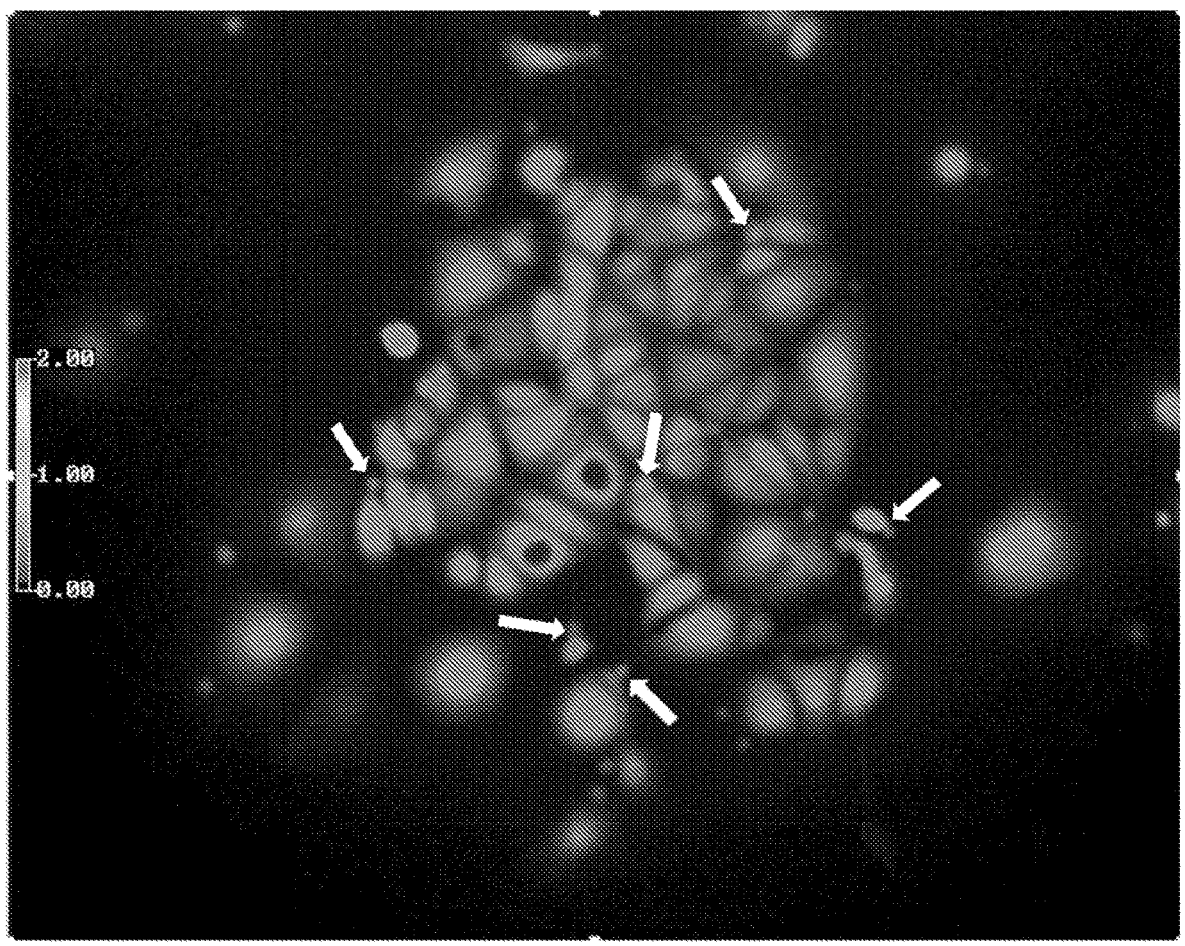
FIG. 11 illustrates emitted fluorescence of DCFDA-loaded MCF-7 cells following flash photolysis of NBA with a 60-30-60 UV flash paradigm. Images were acquired at t=50 minutes. Arrows show the appearance of some somatic blebs, signifying cell death. The scale bar indicates fluorescence ratio measurements below 2.00.

NBA was bath applied to PC12 cells for 10 minutes in order to allow for adequate diffusion across the cell membrane, as previously described. The cells were then exposed to different time paradigms of 350 nm UV light. Flash photolysis of NBA was observed to induce a mean acidosis of 1.18 pH units (n=421; FIG. 8). The magnitude of intracellular acidification can be correlated to the amount of time NBA is exposed to UV light, giving us the ability to control the extent of the induced acidosis (Kohse, J Am Chem Soc. 2013, 135(25):9407-11)(FIG. 15). A single preparation of NBA can induce acidosis multiple times after UV flash photolysis. Experiments were performed in which PC12 cells were observed to undergo changes in $pH_i$ from a physiological range of 7.5 to 3.5 (FIG. 15). The magnitude of intracellular acidification was correlated to the flash photolysis paradigm. We have the ability to induce intracellular acidosis far outside the biological range of cellular activity and optimal intracellular protein function. NBA proton release with UV light is a reproducible and consistent method of inducing acidosis in a system.

Example 4

Figure 5:
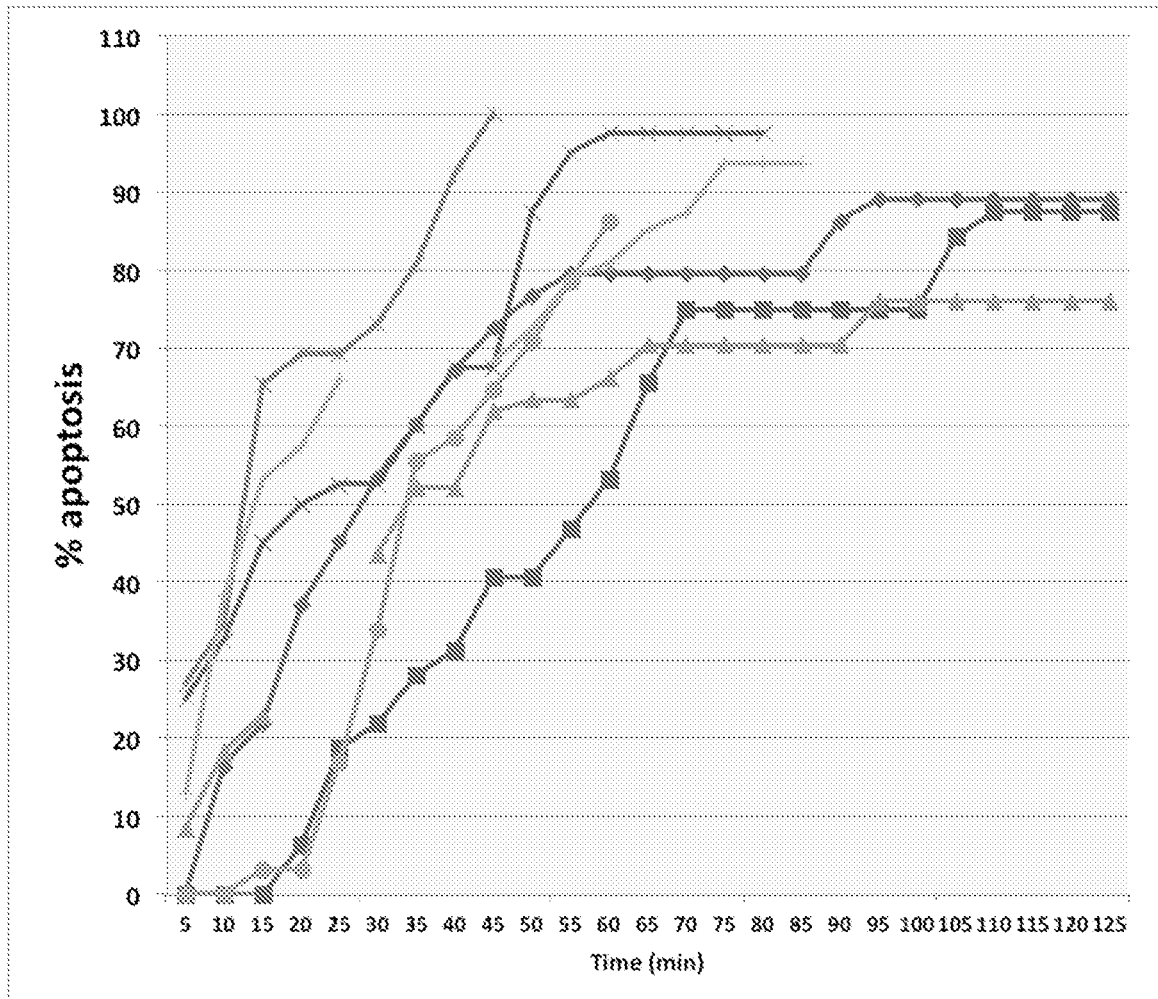
FIG. 5 illustrates the percentage of apoptosis in PC12 cells (n=362) over time in response to focal decreases in pH$_i$ following the uncaging of H$^-$ from NBA (1 mM). Each set of symbols represents a separate experiment after exposure to various UV flash paradigms. These data demonstrate our ability to induce apoptosis in 76 to 100% of cells exposed to pH$_i$-induced apoptosis within 125 minutes.
Figure 6:
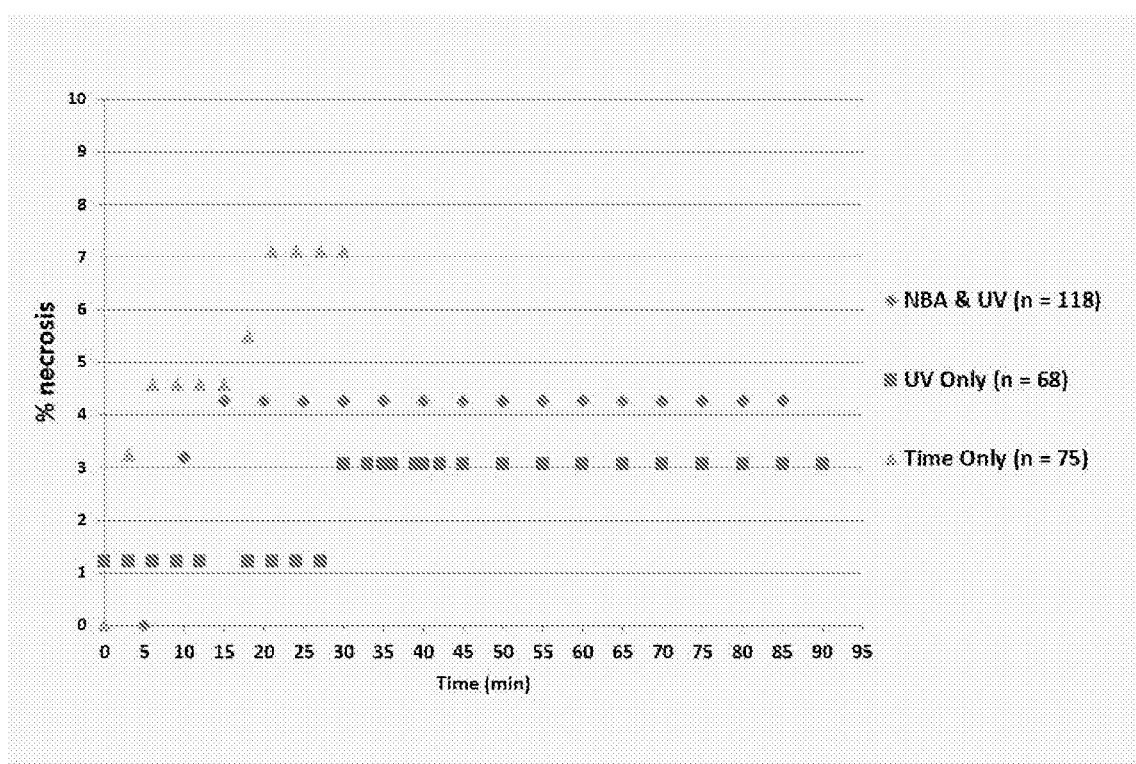
FIG. 6 illustrates the percentage of necrosis in PC12 cells (n=118) over time in response to focal decreases in pH$_i$ following the uncaging of H$^+$ from NBA (1 mM). PC12 cells (n=68) were exposed to a 60-30-60 UV flash paradigm alone, without being loaded with NBA. PC12 cells (n=68) were exposed to UV flash paradigm a without being loaded with NBA. PC12 cells (n=75) were also exposed to time alone with no UV or NBA.

In this embodiment of the invention we prove that intracellular NBA exposed to flash photolysis results in focal cellular damage and death. NBA was allowed to passively diffuse into PC12 cells and exposed to a flash-photolysis paradigm which resulted in the focal release of protons within the cells. DCFDA was used to optically record ratiometric fluorescence in response to induced NBA proton release within the cells. Mean $pH_i$ from before flash photolysis to after flash photolysis was significantly reduced by 1.18 pH units (FIG. 8). Cell death resulting from the significant decreases in $pH_i$ was quantified by fluorescent labeling with Annexin V Alexa Fluor 568 as well as Ethidium Homodimer III, two dyes which discernibly fluoresce in response to apoptosis and necrosis, respectively. The amount of fluorescence due to apoptosis was recorded as a function of time after an acidosis challenge (FIG. 5). Similarly, fluorescence due to necrosis was recorded as a function of time after an acidosis challenge (FIG. 6). The average percent cell death due to apoptosis after flash photolysis of NBA was significantly different from the average percent cell death due to apoptosis in control experiments in which cells were exposed to DCFDA alone, NBA alone, or time alone (FIG. 7).

Figure 7:
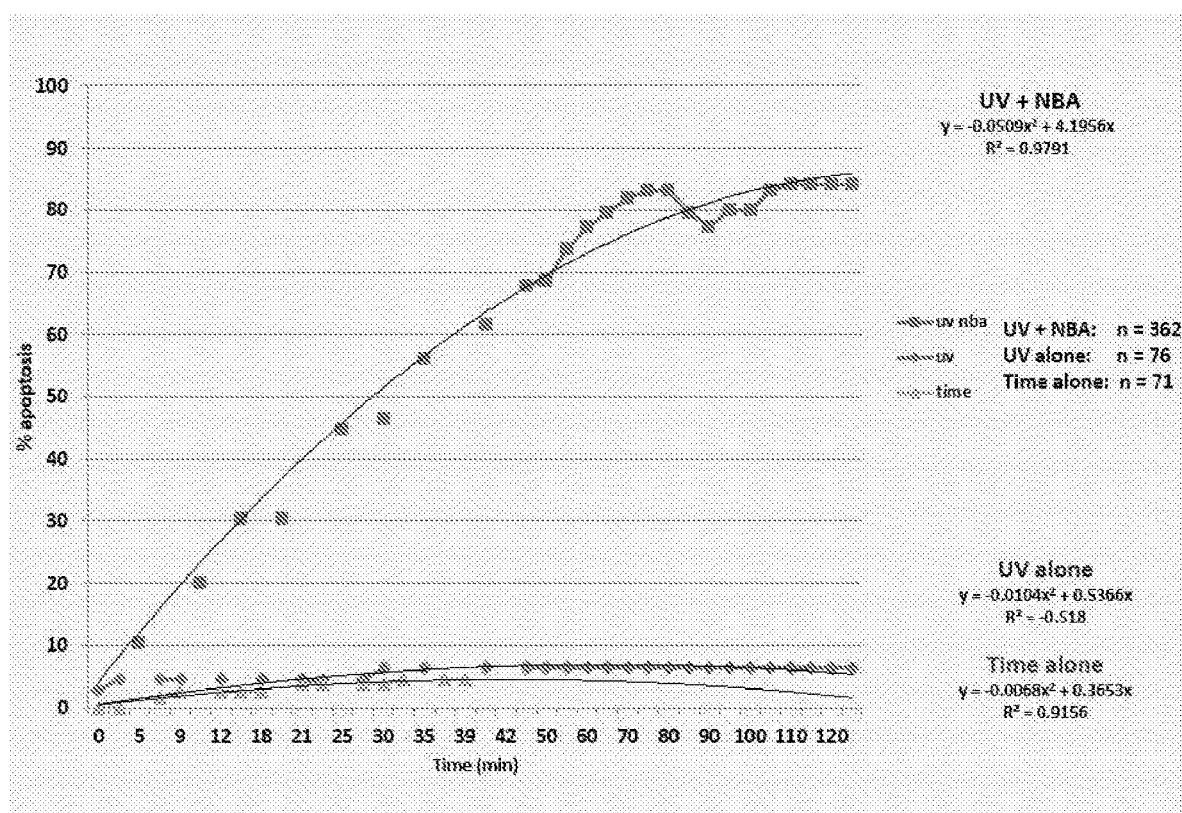
FIG. 7 illustrates a summary of the percentage of apoptosis in PC12 cells (n=362) over time in response to focal decreases in pH$_i$ following the uncaging of H$^+$ from NBA (1 mM) and our control conditions of UV alone (n=76), NBA alone (n=47), and time alone (n=71). There were significant differences between the NBA-UV treated cells and the three control conditions. There were no significant differences between the UV alone, NBA alone, and time alone.

Resulting directly from a focal decrease in $pH_i$ to the point outside of optimum biological range of functionality, PC12 cells exhibited cellular damage and death within 1 to 4 hours of flash photolysis (FIG. 7). This cellular death and damage may be the result of pH-induced damage to cellular organelles and/or via the pH-induced alteration of enzyme function or protein interactions. PC12 cells in control regions not exposed to flash photolysis did not exhibit a significant amount of cellular death (FIG. 7). These data suggest that NBA proton release resulting from UV light exposure is a rapid and focal method of terminating the functional mechanisms of a cell.

Example 5

Figure 12:
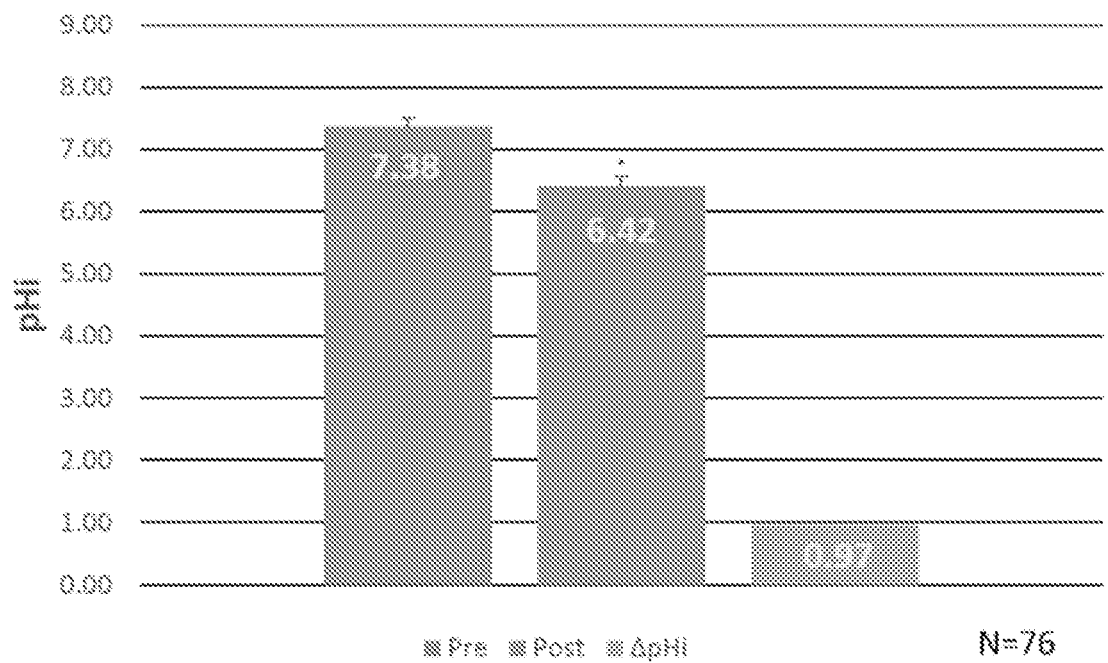
FIG. 12 illustrates mean optical recordings of pH$_i$ from MCF-7 cells (n=76) loaded with 10 µM DCFDA and 1 mM NBA before (7.38 pH$_i$) and after (6.22 pH$_i$) flash photolysis. We were able to induce a significant acidosis (P<0.01) in response to flash photolysis of NBA. The mean change in pH$_i$ (Δ pH$_i$) was 0.97 pH units. The initial pH$_i$ of MCF-7 cells was not significantly different from the pH$_i$ of PC12 cells (see FIG. 8). In addition, the magnitude of acidosis attained in MCF-7 cells (0.97 pH units) was not significantly different from the magnitude of pH$_i$ attained in PC12 cells (1.18 pH units).

Our inventive treatment with NBA causes a drop in intracellular pH ($pH_i$) (FIG. 12) which causes focal and significant cell death in MCF-7 breast cancer cells. This change in $pH_i$ is determined by the amount of time the cells are exposed to UV light once they are treated with NBA, and can produce mild acidosis within biological pH range. Acidosis can also be induced so that the intracellular pH is no longer within a normal biological range (Ravindran, *Journal of Health Care for the Poor and Underserved*, 2011. 22(4):174-186). Control experiments were performed in order to test the toxicity and diffusion of NBA in MCF-7 cells. The $pH_i$ of the cells was monitored with the fluorescent dye DCFDA, with control experiments testing the toxicity of DCFDA alone, NBA alone, UV flash alone. A time control experiment was also conducted in order to determine if the death seen in other controls was due to the time the cultured cells were not in the incubator. After exposing the cells to the experimental conditions and taking recordings for approximately 2 hours, Annexin V Alexa Fluor 568 and optical bleb monitoring were used in order to observe apoptosis. In cells exposed to only one of the conditions, observed apoptosis was minimal compared to the percentages of cells dead or undergoing apoptosis in the cells treated with both NBA and UV (FIG. 13).

Our novel technique will cause rapid, focal decreases in $pH_i$ to induce cell death in cells that excel at evading normal apoptotic mechanisms, such as cancer. Experiments were conducted in order to show that focal intracellular acidification would be sufficient to induce cell death, a feat that has to date evaded cancer researchers. In MCF-7 cells that were exposed to treatment, their cellular membranes did not go through normal apoptosis mechanisms that would have resulted in membrane inversion, allowing apoptosis to be monitored with Annexin V. In the case of the cancer cells, the membranes swelled in various areas and showed cellular blebbing, a phenomenon that was not seen in the PC12 experiments. The literature surrounding the mechanism of bleb formation is limited, however it has been reported that cellular blebbing was a sign of irreversible processes that resulted in cell death (Andrade et al., *Biology of the Cell*, 2010, 102(1):25-35). Therefore in many of the MCF-7 experiments, the appearance of blebs was used in conjunction with Annexin V in order to determine the percentage of cell death.

Figure 13:
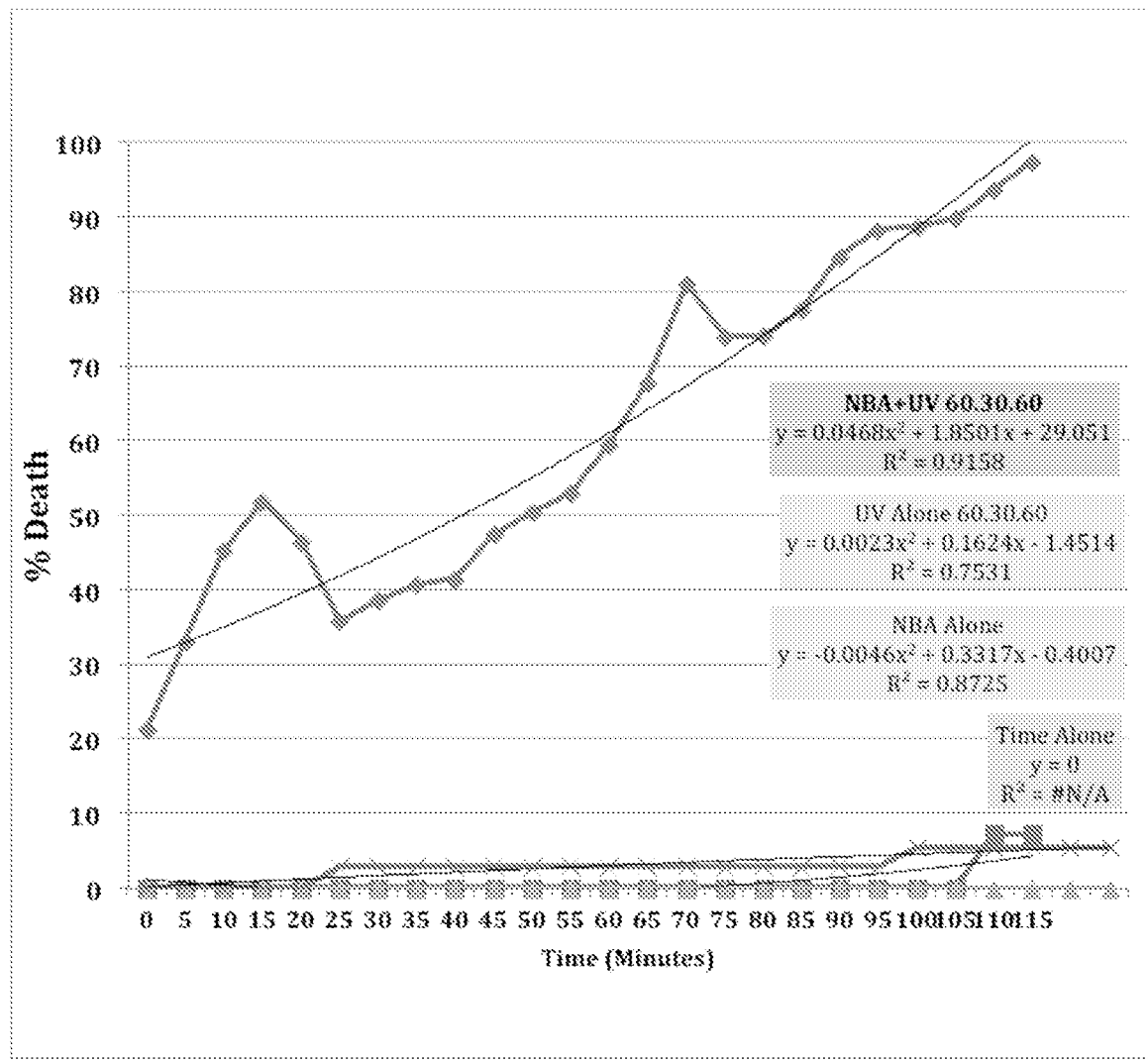
FIG. 13 illustrates the mean percentage of MCF-7 cell death, indicated by blebbing or Annexin V fluorescence, by condition. MCF-7 cells (n=262) were loaded with 1 mM NBA and subsequently exposed to a 60-30-60 UV flash paradigm. As separate controls MCF-7 cells were exposed to a 60-30-60 UV flash paradigm alone (n=112), NBA alone (n=47), or time alone (n=20). Linear regression analyses indicate apoptosis and cell death with treatment of MCF-7 cells with NBA and UV light was significantly greater than our controls.

Our results showed a focal, controlled, and extremely quick death process (FIG. 13). Once the cells incubated in NBA were exposed to UV, significant drops in pH, outside of physiological range, cellular blebbing, and morphological changes were seen in minutes, with percentages of death above 90% within 2 hours. Cells that were exposed to NBA but not the UV flash (control regions) had pH, values in the normal physiological range, while neighboring cells exposed to UV underwent cellular blebbing and showed apoptosis when imaged with Annexin V. This cellular death and damage may be the result of pH-induced damage to cellular organelles and/or via the pH-induced alteration of enzyme function or protein interactions. Control regions were evaluated in the same 35 mm dish as the treated cells, approximately 10 mm away from the area of treatment. Despite the proximity to the treated area, control regions did not show the levels of apoptosis seen in the treated areas (FIG. 13), exhibiting the focal nature of these treatments.

Example 6

Our inventive treatment with NBA causes a drop in intracellular pH ($pH_i$) which causes focal and significant cell death in the highly aggressive triple negative MDA-MB-231 breast cancer cells. This change in $pH_i$ is determined by the amount of time the cells are exposed to UV light once they are treated with NBA, and can produce mild acidosis within biological pH range, or severe acidosis which is outside the physiological range. We demonstrate the ability to induce apoptosis and cell death in 55.3% the aggressive triple negative breast cancer exposed to an NBA and flash photolysis paradigm which caused a significant decrease in pHi of 3.68±0.18 pH units (P<0.001).

Example 7

Our described inventive treatment of cells invokes a novel, positive feedback system which facilitates cell death, and that this positive feedback pathway could serve as an advantageous mechanism induce cell death in any cell demonstrating a resistance to common therapies, such as multidrug resistant cancers and antibiotic resistant bacteria.

Figure 2:
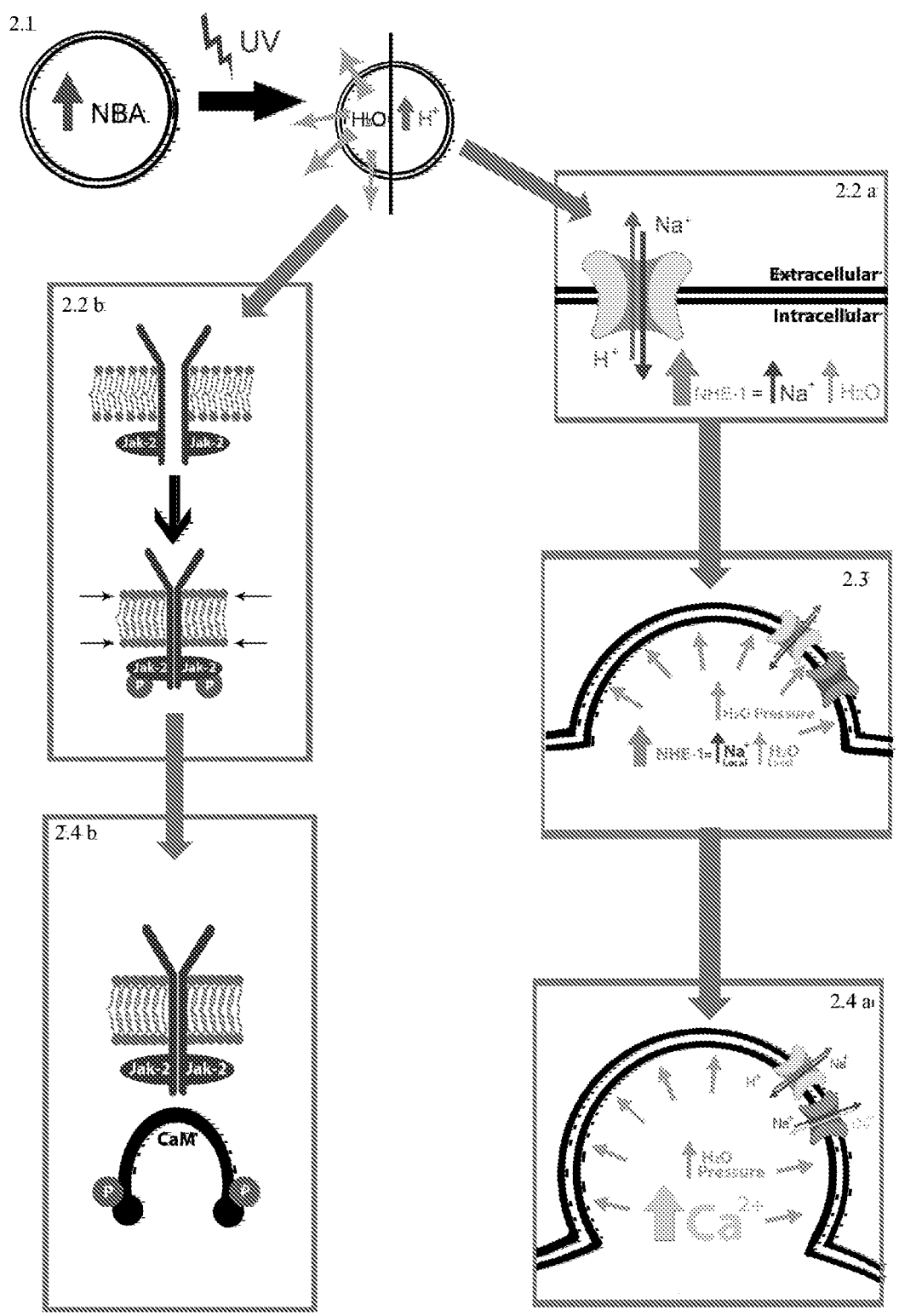
FIG. 2 is a diagram of the proposed positive feedback pathway in MCF-7 cells, which occurs following significant increases in intracellular $H^+$ from NBA in response to a UV flash. 2.1 illustrates the exposure of intracellular NBA to 350 nm wavelength UV flash paradigm, causing a sudden increase in proton concentration in the intracellular space. This intracellular acidification results in the concomitant osmotic water loss or change in cell volume. The increase in intracellular $H^+$ activates NHE1 to extrude protons in exchange for sodium ions (2.2a). Sodium ions act as osmolites, drawing water to the area of high sodium concentration inside the cell. The movement of water to the area of high $Na^+$, or the extrusion of water, leads to a deformation of the cell wall and/or cell shrinkage. The deformation of the cell wall results in phosphorylation and activation of the tyrosine kinase Janus kinase II (Jak-2) (Garnovskaya et al., *J Biol Chem*. 2003, 278(19): 16908-15)(2.2b). The continued activation of NHE1 in response to the intracellular $H^+$ creates increases in intracellular osmotic pressure, resulting in an outward protrusion on the cellular membrane, or a bleb (2.3). The activity of NHE1 attempts to compensate for the focal acidosis inside the cell, causing intracellular $Na^+$ levels to rise, further promoting the hydrostatic pressure within, and subsequent size of the bleb. In response to the local increase in intracellular $Na^+$ concentration, the sodium calcium exchanger 1 (NCX1) reverses exchange activity (Yi et al., *J. Biol Chem*. 2012, 287(13):10316-24), leading to the efflux of $Na^+$ and influx of $Ca^{2+}$ (2.4a). Complexation of phosphorylated Jak-2 and calmodulin (CaM; 2.4b) increases the Jak-2-dependent tyrosine phosphorylation of CaM. The increase in intracellular $Ca^{2+}$ via the reversal of NCX1 facilitates the binding of $Ca^{2+}$ to calmodulin, independent of the phosphorylation state of CaM. While both phosphorylated CaM (Garnovskaya et al., *J Biol Chem*. 2003, 278(19): 16908-15) and calcified CaM (Köster et al., *J Biol Chem*. 2011, 286(47): 40954-61) increase the activity of NHE1, the combination of phosphorylation and calcification of CaM (2.5) imparts the highest affinity of CaM to NHE1 (Köster et al., *J Biol Chem*. 2011, 286(47): 40954-61)(2.6a), and thereby promotes the greatest activation of NHE1 (Köster et al., *J Biol Chem*. 2011, 286(47): 40954-61). In spite of $Na^+$ extrusion via NCX1, maintained activation of NHE1 is facilitated by the phosphorylated-calcified CaM, leading to further Ca$^{2+}$ entry (2.6b and 2.6c). The suprophysiological increases in intracellular H$^+$ induced by flash photolysis of NBA leads to cell shrinkage followed by subsequent activation of NHE1, Jak-2, and NCX1; creating a novel pathway of positive feedback. This ultimately leads to increased intracellular osmotic pressure, cellular blebs, and potential rupture of the cell membrane.
Figure 2:
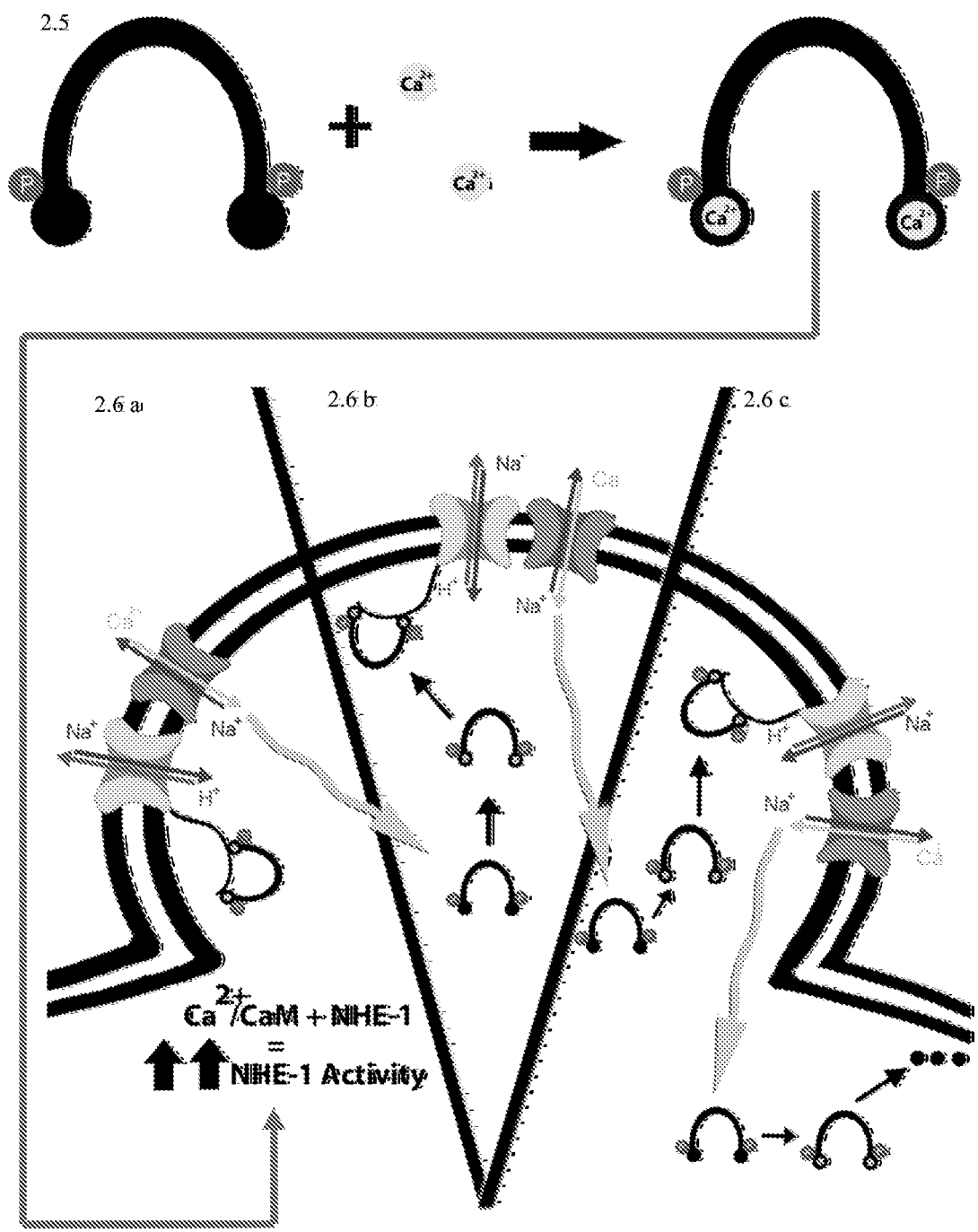

The described positive feedback pathway in MCF-7 cells, which occurs following significant increases in intracellular H from NBA in response to a UV flash. FIG. 2.1 illustrates the exposure of intracellular NBA to 350 nm wavelength UV flash paradigm, causing a sudden increase in proton concentration in the intracellular space and concomitant osmotic water loss or change in cell volume. The increase in intracellular H activates NHE1 to extrude protons in exchange for sodium ions (FIG. 2.2a). Sodium ions act as osmolites, drawing water to the area of high sodium concentration inside the cell. The movement of water to the area of high $Na^+$, or the extrusion of water leads to a deformation of the cell wall and/or cell shrinkage. The deformation of the cell wall results in phosphorylation and activation of the tyrosine kinase Jak-2 (Garnovskaya et al., *J Biol Chem.* 2003, 278(19):16908-15)(FIG. 2.2b). The continued activation of NHE1 in response to the intracellular $H^+$ creates increases in intracellular osmotic pressure, resulting in an outward protrusion on the cellular membrane, or a bleb (FIG. 2.3). The activity of NHE1 attempts to compensate for the focal acidosis inside the cell, causing intracellular $Na^+$ levels to rise, further promoting the hydrostatic pressure within, and subsequent size of the bleb. In response to the local increase in intracellular $Na^+$ concentration, the sodium calcium exchanger 1 (NCX1) reverses exchange activity (Yi et al., *J. Biol. Chem.* 2012, 287(13):10316-24), leading to the efflux of $Na^+$ and influx of $Ca^{2+}$ (FIG. 2.4a). Complexation of phosphorylated Jak-2 and calmodulin (CaM; FIG. 2.4b) increases the Jak-2-dependent tyrosine phosphorylation of CaM. Phosphorylated CaM binds to the C-terminus of NHE1, constitutively activating NHE1 (Garnovskaya et al., *J Biol Chem.* 2003, 278(19):16908-15). The increase in intracellular $Ca^{2+}$ via the reversal of NCX1 facilitates the binding of $Ca^{2+}$ to calmodulin, independent of the phosphorylation state of CaM. While both phosphorylated CaM (Garnovskaya et al., *J Biol Chem.* 2003, 278(19):16908-15) and calcified CaM (Köster et al., *J Biol Chem.* 2011, 286(47):40954-61) increase the activity of NHE1, the combination of phosphorylation and calcification of CaM (FIG. 2.5) imparts the highest affinity of CaM to NHE1 (Köster et al., *J Biol Chem.* 2011, 286(47):40954-61; (FIG. 2.6a), and thereby promotes the greatest activation of NHE1 (Köster et al., *J Biol Chem.* 2011, 286(47):40954-61). In spite of $Na^+$ extrusion via NCX1, maintained activation of NHE1 is facilitated by the phosphorylated-calcified CaM, leading to further $Ca^{2+}$ entry (FIGS. 2.6b and 2.6c). We propose that the supraphysiological increases in intracellular $H^+$ induced by flash photolysis of NBA leads to cell shrinkage followed by subsequent activation of NHE1, Jak-2, and NCX1; creating a novel pathway of positive feedback, this ultimately leads to increased intracellular osmotic pressure, cellular blebs, and potential rupture of the cell membrane. We propose this positive feedback pathway will also be effective in killing multidrug resistant cancer, especially given the increased expression of NHE1 in multidrug resistant cancer (Hoffman and Lambert, *Philosophical Transactions of the Royal Society London Biological Sciences,* 2014, 369 (1638):20130109).

Example 8

Our described inventive treatment will allow us to produce modest, incremental, and precise decreases in $pH_i$ alone and correlate the magnitude of change in pH, to the percent yield of reprogramming mouse splenic $CD45^+$ cells to a pluripotent state.

Example 9

Our inventive technique is effective in significantly decreasing the growth of cancerous tumors in vivo. We injected the aggressive triple negative breast cancer MDA-MB-231-GFP ($2\times10^6$ cells) into the mammary fat pad of 5 week old female nude mice. Tumors appeared after approximately one week following injection. Treatment was initiated once the tumors reached and maintained a length of 5 mm for two consecutive days. The mice received a one-time treatment of either a control injection if 0.1 ml of aCSF to the tumor or 0.1 ml of NBA (1 mM) followed by photoactivation. The NBA/photoactivation treatment was conducted as follows: one hour after NBA injection, the animal was anesthetized (1.5-4% isoflurane) prior to the insertion of a 200 μm fiber optic cannula into the tumor mass. The interior of the tumor was illuminated with 405 nm light (80-85 mW) via a ceramic cannula using the same illumination paradigm which was effective in vitro, specifically 60 seconds of illumination, 60 seconds of no illumination, 30 seconds of illumination, 60 seconds of no illumination, and 60 seconds of illumination. This paradigm is referred to as a "60-30-60" illumination paradigm.

Tumors were measured daily in order to calculate changes in tumor volume using the formula:

Tumor Volume(TV)=Length×width/2

Figures 19A, 19B:
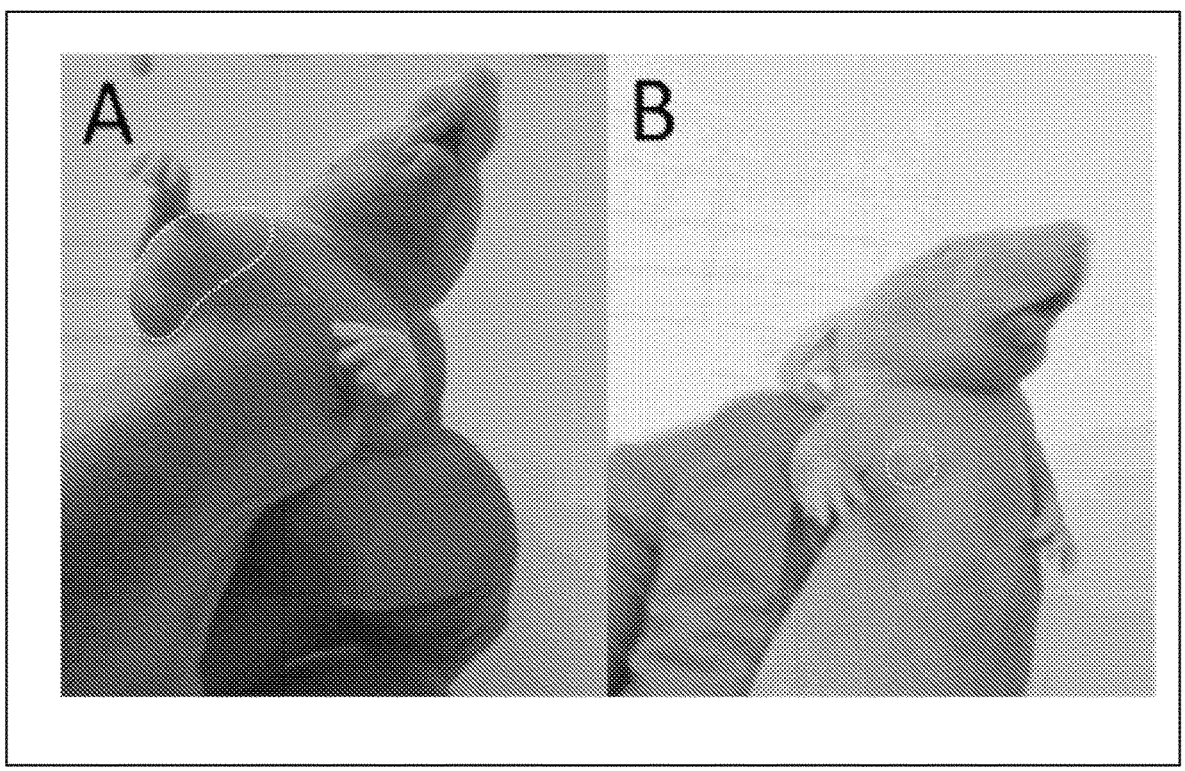
FIG. 19 illustrates the triple negative breast cancer MDA-MB-231 tumors in a control mouse 5 days after a 0.1 ml aCSF injection (A) and an NBA-phototherapy mouse 3 days after 0.1 ml 1 mM NBA and phototherapy. The margins of the tumor are outlined with a yellow dashed line.
Figure 20:
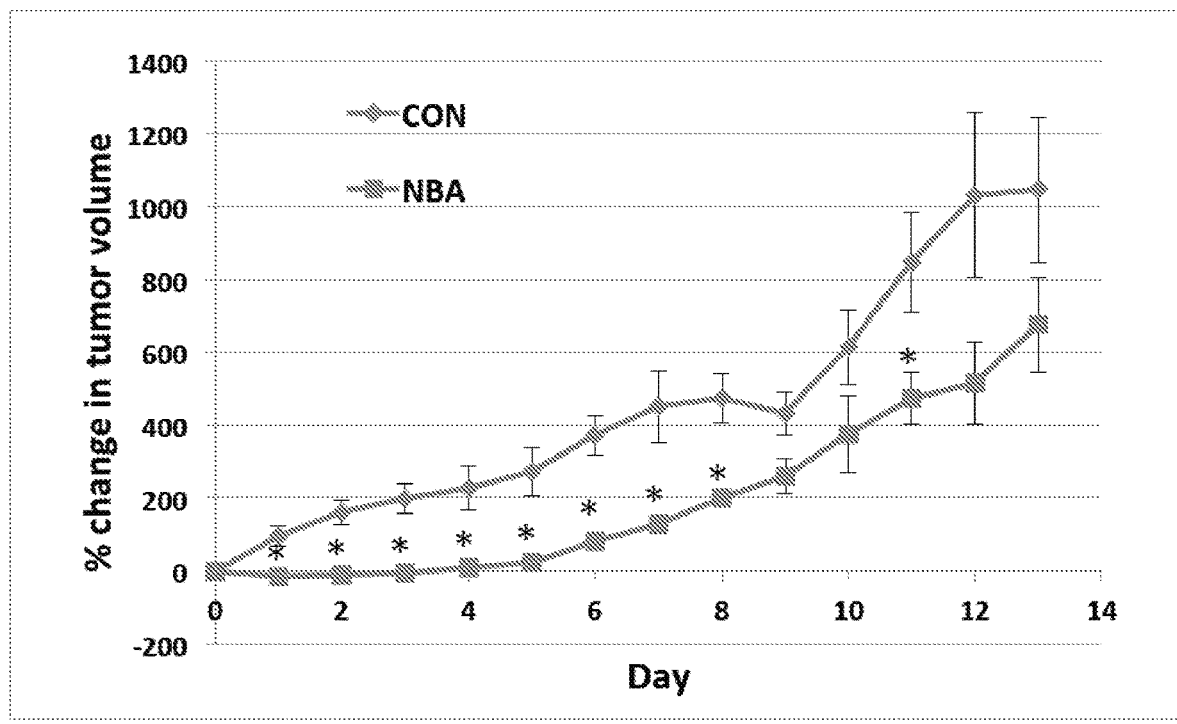
FIG. 20 illustrates the significant decreases in the percent change in tumor volume in NBA-phototherapy (NBA) treated mice when compared to control aCSF (CON) treated mice. The percent change in tumor volume was normalized in each animal to the tumor volume on the day of treatment. The one-time treatment of NBA induced significant decreases in the percent change in tumor volume for up to 9 continuous days.
Figure 21:
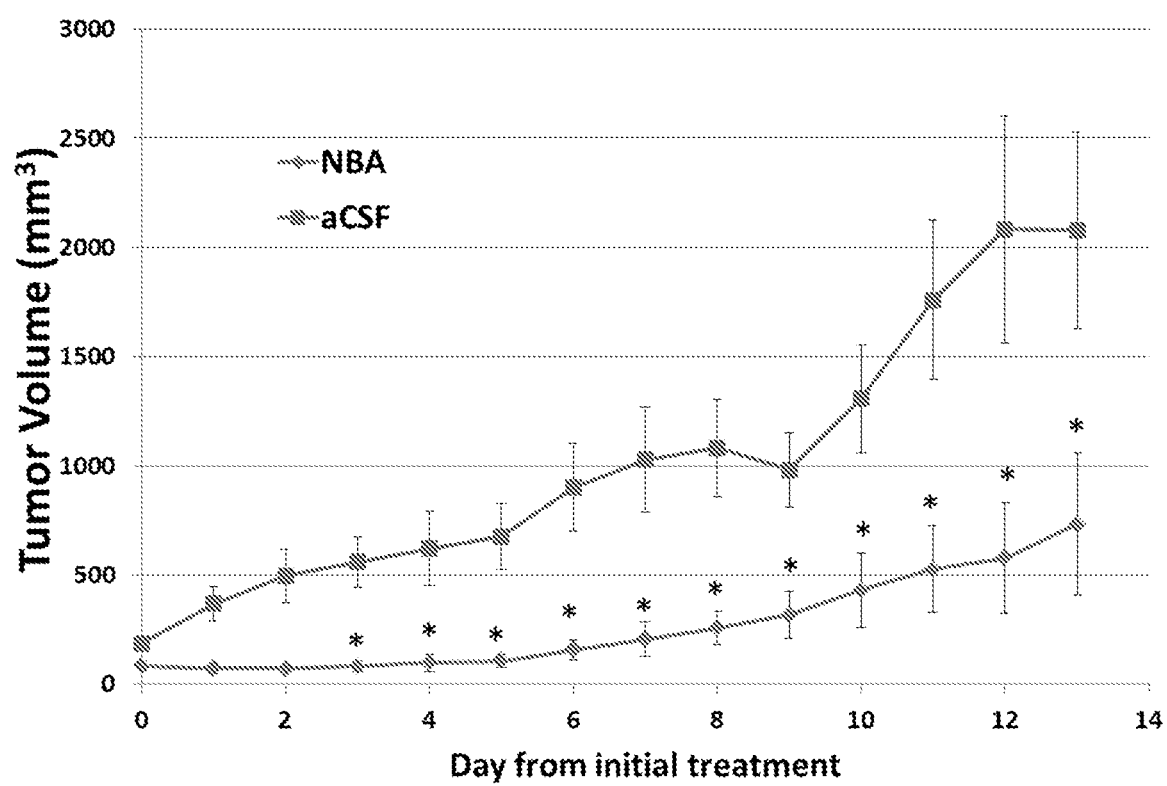
FIG. 21 illustrates the significant decreases in tumor volume ($mm^3$) in NBA-phototherapy (NBA) treated mice when compared to control aCSF (CON) treated mice. The one-time treatment of NBA induced significant decreases in the tumor volume from the second day post-treatment for up to 13 days post treatment. The significant reduction in tumor volume in NBA treated animals compared to control ended at day 14 because day 14 represented the beginning of the control animals being euthanized in response to reaching humane endpoints.

The percent change in tumor volume was calculated by normalizing the percent change to the tumor volume recorded on the day of treatment. Digitial Vernier calipers were used to perform daily tumor measurements from control and NBA phototreated mice. We observed significant reductions in the growth of tumors in MBA treated mice (FIG. 19). Statistical analyses indicate that the one-time treatment of the tumors by NBA phototherapy produced significant reductions the percent change in tumor growth (FIG. 20) and in tumor volume (FIG. 21). The one-time NBA phototherapy produced significant reductions in percent change in tumor growth from the treatment day when compared to the mean percent change in tumor growth in control aCSF treated mice (FIG. 20). This "complete response" of the reduction in the mean percent change in tumor volume was significantly reduced (P<0.05) for up to nine days.

The one-time NBA phototherapy produced significant reductions in tumor volume from the treatment day when compared to the tumor volume in control aCSF treated mice (FIG. 21). This "complete response" of the reduction in the mean tumor volume was significantly reduced (P<0.05) for up to 13 days.

Example 10

The described inventive technique is effective in increasing the duration of survival in animals with cancer in vivo. In this embodiment of the invention, we prove that employing the technique to photoactivate NBA in cancer tumors leads to significant increases in animal survival. NBA was injected into the established triple negative breast cancer MDA-MB-231 tumors of 6 week old nude mice. One hour was permitted to allow adequate diffusion of the NBA into the intracellular space of the cancer cells. Following this one-hour diffusion period, the tumors were exposed to 405 nm photo-activating light (85 mW) for a 60-30-60 excitation paradigm (described previously).

Figure 22:
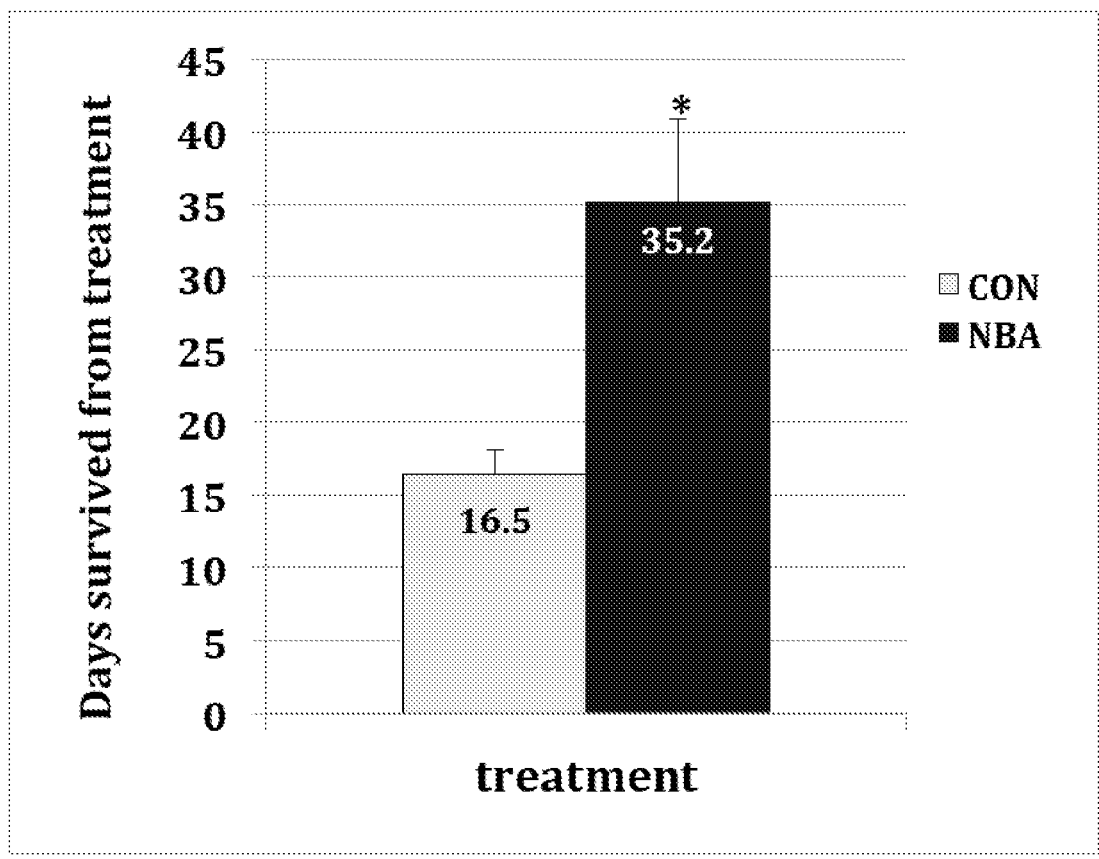
FIG. 22 illustrates the significant increase in survival in vivo of our novel NBA photodynamic therapy. Aggressive triple negative MDA-MB-231 human breast cancer tumors in nude mice were give a one-time treatment of either control aCSF (CON) or NBA photodynamic therapy (NBA). The mean days survived (±1 SEM) were significantly larger in NBA treated mice when compared to control mice.

Following their one-time treatment of either NBA with photo-activation or control aCSF, mice were monitored and euthanized in accordance with the Humane Endpoints approved by the University of Texas at San Antonio Institutional Animal Care and Use Committee (IACUC). The control aCSF treated mice (n=4) survived for an average of 16.5±1.66 days from the day of treatment, with survival days from treatment ranging from 14 to 19 days. In contrast, the one-time NBA treated mice survived for 35.2±5.70 days from the day of treatment (FIG. 22). The NBA treated mice survival ranged from 18 to 50 days from treatment. This increase in survival represents a significant (P=0.012) 113.3% increase in survivability as a result of the inventive NBA treatment.

The invention claimed is:

1. A method for treating a cancerous tumor in a patient comprising (i) administering 2-nitrobenzaldehyde to the cancerous tumor in the patient, wherein the 2-nitrobenzaldehyde is internalized by a cancerous tumor cell forming a 2-nitrobenzaldehyde containing cancer cell, and (ii) irradiating the tumor having 2-nitrobenzaldehyde containing cancer cell with a light source to reduce the internal pH of the 2-nitrobenzaldehyde containing cancer cell below 6.4 and inducing cell death in response to cellular acidosis of the 2-nitrobenzaldehyde containing cancer cell and treating the tumor.

2. The method of claim 1, wherein the light source produces light having a wavelength of 350 nm.

3. The method of claim 1, wherein the light source is exposed in a series of three flashes with a duration of 60 seconds, 30 seconds, and 60 seconds, with 2 minute intervals between each flash.

4. The method of claim 1, wherein 2-nitrobenzaldehyde is coupled to a nanoparticle.

5. The method of claim 4, wherein the nanoparticle is coupled to a cancer targeting agent.

6. The method of claim 5, wherein 2-nitrobenzaldehyde is coupled to a cancer targeting agent.

7. The method of claim 1, further comprising administering a second cancer therapy.

8. A method for inducing cell death in response to cellular acidosis of a tumor cell comprising (i) administering 2-nitrobenzaldehyde to a tumor cell where it is internalized by the tumor cell, and (ii) irradiating the tumor cell with a light source to reduce the pH of said cell below 6.4.

9. The method of claim 8, wherein the light source has a wavelength of 350 nm.

10. The method of claim 8, wherein the light source is exposed in a series of three flashes with a duration of 60 seconds, 30 seconds, and 60 seconds, with 2 minute intervals between each flash.

11. The method of claim 8, wherein 2-nitrobenzaldehyde is coupled to a nanoparticle.

12. The method of claim 11, wherein the nanoparticle is coupled to a targeting agent.

13. The method of claim 8, wherein 2-nitrobenzaldehyde is coupled to a targeting agent.

14. The method of claim 1, wherein the light source produces light having a wavelength of 200 to 400 nm.

* * * * *